(12) United States Patent
Serruto et al.

(10) Patent No.: US 10,179,167 B2
(45) Date of Patent: Jan. 15, 2019

(54) DEVELOPMENTS IN MENINGOCOCCAL OUTER MEMBRANE VESICLES

(71) Applicant: GlaxoSmithKline Biologicals SA, Rixensart (BE)

(72) Inventors: Davide Serruto, Siena (IT); Mariagrazia Pizza, Siena (IT); Isabel Delany, Siena (IT)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 0 days.

(21) Appl. No.: 14/989,737

(22) Filed: Jan. 6, 2016

(65) Prior Publication Data
US 2016/0199476 A1   Jul. 14, 2016

Related U.S. Application Data

(62) Division of application No. 13/822,238, filed as application No. PCT/IB2011/053957 on Sep. 9, 2011, now Pat. No. 9,259,462.

(60) Provisional application No. 61/429,673, filed on Jan. 4, 2011, provisional application No. 61/381,859, filed on Sep. 10, 2010.

(51) Int. Cl.
| | | |
|---|---|---|
| A61K 39/00 | (2006.01) | |
| A61K 39/095 | (2006.01) | |
| A61K 49/00 | (2006.01) | |
| C12N 9/10 | (2006.01) | |
| C07K 14/22 | (2006.01) | |
| C12N 1/20 | (2006.01) | |
| C12N 1/38 | (2006.01) | |

(52) U.S. Cl.
CPC ............ *A61K 39/095* (2013.01); *C07K 14/22* (2013.01); *C12N 1/20* (2013.01); *C12N 1/38* (2013.01); *C12N 9/1085* (2013.01); *A61K 2039/523* (2013.01); *C12Y 205/01072* (2013.01)

(58) Field of Classification Search
CPC ....... A61K 39/00; A61K 39/095; A61K 49/00
USPC .................. 424/9.1, 9.2, 200.1, 234.1, 249.1
See application file for complete search history.

(56) References Cited

U.S. PATENT DOCUMENTS

| | | | |
|---|---|---|---|
| 5,547,670 A | 8/1996 | Goldstein et al. | |
| 6,013,267 A | 1/2000 | Blake et al. | |
| 6,028,049 A | 2/2000 | Jacobs et al. | |
| 6,180,111 B1 | 1/2001 | Stein et al. | |
| 6,197,312 B1 | 3/2001 | Peak et al. | |
| 6,355,253 B1 | 3/2002 | Zlotnick | |
| 6,451,317 B1 | 9/2002 | Milan et al. | |
| 6,709,660 B1 | 3/2004 | Scarlato et al. | |
| 6,914,131 B1 | 7/2005 | Scarlato et al. | |
| 6,936,261 B2 | 8/2005 | Granoff et al. | |
| 7,018,636 B1 | 3/2006 | Bhattacharjee et al. | |
| 7,189,554 B2 | 3/2007 | Apicella et al. | |
| 7,348,006 B2 | 3/2008 | Contorni et al. | |
| 7,368,261 B1 | 5/2008 | Rappuoli | |
| 7,384,645 B2 | 6/2008 | Foster et al. | |
| 7,576,176 B1 | 8/2009 | Fraser et al. | |
| 7,604,810 B2 | 10/2009 | Rappuoli | |
| 7,628,995 B2 | 12/2009 | Bos et al. | |
| 7,731,967 B2 | 6/2010 | O'Hagan et al. | |
| 7,754,218 B2 | 7/2010 | Contorni et al. | |
| 7,838,014 B2 | 11/2010 | Biemans et al. | |
| 7,838,015 B2 | 11/2010 | O'Hagan et al. | |
| 7,862,827 B2 | 1/2011 | Giuliani et al. | |
| 7,939,087 B2 | 5/2011 | Telford et al. | |
| 8,007,815 B1 | 8/2011 | Granoff et al. | |
| 8,029,807 B2 | 10/2011 | Bos et al. | |
| 8,114,960 B2 | 2/2012 | Arico et al. | |
| 8,529,906 B2 | 9/2013 | O'Hagan et al. | |
| 8,663,656 B2 | 3/2014 | Pizza | |
| 8,703,914 B2 | 4/2014 | Arico et al. | |
| 8,758,764 B2 | 6/2014 | Masignani et al. | |
| 8,765,135 B2 | 7/2014 | Contorni | |
| 8,808,711 B2 | 8/2014 | Oster et al. | |
| RE45,137 E | 9/2014 | O'Hagan et al. | |
| 8,968,748 B2 | 3/2015 | Granoff et al. | |
| 8,980,277 B2 | 3/2015 | Pizza | |
| 9,011,869 B2 | 4/2015 | Pizza | |
| 9,139,621 B2 | 9/2015 | Fraser | |
| 2002/0160016 A1 | 10/2002 | Peak et al. | |
| 2004/0092711 A1 | 5/2004 | Arico | |
| 2004/0110670 A1 | 6/2004 | Arico et al. | |
| 2005/0232936 A1 | 10/2005 | Arico et al. | |
| 2006/0029621 A1 | 2/2006 | Granoff et al. | |
| 2006/0051379 A1* | 3/2006 | Biemans ............... | A61K 39/095 424/249.1 |
| 2006/0051840 A1 | 3/2006 | Arico et al. | |
| 2006/0166344 A1 | 7/2006 | Pizza et al. | |
| 2006/0171957 A1 | 8/2006 | Pizza | |
| 2006/0240045 A1 | 10/2006 | Berthet et al. | |
| 2007/0059329 A1 | 3/2007 | Norals et al. | |
| 2007/0082014 A1 | 4/2007 | Costantino | |

(Continued)

FOREIGN PATENT DOCUMENTS

| | | |
|---|---|---|
| EP | 0011243 B1 | 4/1982 |
| EP | 0273116 A2 | 7/1988 |

(Continued)

OTHER PUBLICATIONS

Schielke, S., et al. Molecular Microbiology, vol. 72, No. 4, pp. 1054-1067, published online Apr. 29, 2009.*

(Continued)

*Primary Examiner* — Rodney P Swartz

(57) ABSTRACT

A first aspect of the invention provides meningococcal outer membrane vesicles in which NHBA is over-expressed. A second aspect of the invention provides meningococcal outer membrane vesicles in which NadA is over-expressed. A third aspect of the invention provides a panel of bacterial strains, each member of which is isogenic except for a single gene which in each strain encodes a different variant antigen of interest.

21 Claims, 13 Drawing Sheets

Specification includes a Sequence Listing.

(56) References Cited

U.S. PATENT DOCUMENTS

| | | | |
|---|---|---|---|
| 2009/0035328 A1* | 2/2009 | Granoff | A61K 39/095 424/200.1 |
| 2009/0221045 A1 | 9/2009 | Morishige et al. | |
| 2009/0232820 A1 | 9/2009 | Fraser et al. | |
| 2010/0267931 A1 | 10/2010 | Arico et al. | |
| 2011/0182942 A1 | 7/2011 | Zollinger | |
| 2011/0262484 A1 | 10/2011 | Feavers | |
| 2012/0263753 A1 | 10/2012 | O'Hagan et al. | |
| 2013/0236489 A1 | 9/2013 | Serruto et al. | |
| 2014/0037668 A1 | 2/2014 | Giuliani et al. | |

FOREIGN PATENT DOCUMENTS

| | | |
|---|---|---|
| EP | 0467714 A1 | 1/1992 |
| EP | 1741443 B1 | 10/2007 |
| EP | 1790660 B1 | 6/2012 |
| NL | 8901612 A | 7/1990 |
| WO | WO-90/06696 A2 | 6/1990 |
| WO | WO-92/16643 A1 | 10/1992 |
| WO | WO-95/33049 A2 | 12/1995 |
| WO | WO-96/29412 A1 | 9/1996 |
| WO | WO-97/13860 A1 | 4/1997 |
| WO | WO-99/24578 A2 | 5/1999 |
| WO | WO-99/36544 A2 | 7/1999 |
| WO | WO-99/57280 A2 | 11/1999 |
| WO | WO-99/61053 A1 | 12/1999 |
| WO | WO-00/22430 A2 | 4/2000 |
| WO | WO-00/66741 A2 | 11/2000 |
| WO | WO-00/66791 A1 | 11/2000 |
| WO | WO-00/71725 A2 | 11/2000 |
| WO | WO-01/31019 A2 | 5/2001 |
| WO | WO-01/34642 A2 | 5/2001 |
| WO | WO-01/52885 A1 | 7/2001 |
| WO | WO-01/64920 A2 | 9/2001 |
| WO | WO-01/64922 A2 | 9/2001 |
| WO | WO-01/91788 A1 | 12/2001 |
| WO | WO-02/09643 A2 | 2/2002 |
| WO | WO-03/009869 A1 | 2/2003 |
| WO | WO-03/010194 A2 | 2/2003 |
| WO | WO-03/020756 A2 | 3/2003 |
| WO | WO-04/014417 A2 | 2/2004 |
| WO | WO-04/014418 A2 | 2/2004 |
| WO | WO-2004/019977 A2 | 3/2004 |
| WO | WO-04/032958 A1 | 4/2004 |
| WO | WO-04/048404 A2 | 6/2004 |
| WO | WO-04/054611 A1 | 7/2004 |
| WO | WO-2005/004908 A1 | 1/2005 |
| WO | WO-2005/064021 A2 | 7/2005 |
| WO | WO-05/106009 A2 | 11/2005 |
| WO | WO-2006/046143 A2 | 5/2006 |
| WO | WO-2007/144316 A2 | 12/2007 |
| WO | WO-2009/158142 A1 | 12/2009 |

OTHER PUBLICATIONS

"VA-MENGOC-BC," Product information from S.C.S. Farmacia Manes, Argentina. Cited in International Search Report for PCT/US99/11977 dated May 28, 1999. 1 page.

Adu-Bobie, J. et al. (2004)"GNA33 of Neisseria meningitidis is a lipoprotein required for cell separation, membrane architecture, and virulence" Infection and Immunity 72(4):1914-1919.

Arigita, C. at al. "Stability of mono- and trivalent meningococcal outer membrane vesicle vaccines," Vaccine, vol. 22, No. 5-0, 2004, pp. 630-643.

Ballard, TL et al, Nov. 1985, Journal of Clinical Microbiology, vol. 22(5), pp. 754-756, Clinically significant Cross-reactions with Counterimmunoelectrophoresis between Pneumonococcus Type 6 and Haemophilus influenzae type b.

Bjune et al., "Effect of outer membrane vesicle vaccine against group B meningococcal disease in Norway," Lancet 338(8775):1093-1096,1991.

Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.

CECMED (Dec. 2, 2011), "Resumen de las Caracteristicas del Producto: VA-MENGOC-BC," Ministerio de Salud Publica de Cuba, 4 pages. (3 page English translation included).

Collins (2011). "Gram-negative outer membrane vesicles in vaccine development," Discov Med, 12(62):7-15.

Corbel, "Control testing of combined vaccines: a consideration of potential problems and approaches," Biologicals 22(4):353-360, 1994.

Dalseg et al. (May 14, 1999). "Outer membrane vesicles from group B meningococci are strongly immunogenic when given intranasally to mice" Vaccine 17(19):2336-2345.

De Kleijn, ED. et al. "Immunogenicity and safety of a hexavalent meningococcal outer membrane-vesicle vaccine in children of 2-3 and 7-8 years of age," Vaccine, 18:1456-1466(2000).

De Moraes JC, et al. (1992). Protective efficacy of a serogroup B meningococcal vaccine in Sao Paulo, Brazil. Lancet 340: 1074-1078.

Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).

Debbag et al., "Evaluation of Adverse Reactions Associated to Antimeningococcal BC Vaccination in 16,700 Children" Clinical Infectious Diseases, vol. 21, pp. 790-A420 (Sep. 1995).

Decision revoking EP1644035, filed in Opposition against EP1644035, dated Jan. 20, 2014, 14 pages.

Declaration from Christiane Feron, filed in opposition against EP1534326, dated Sep. 28, 2009, 3 pages.

Devoe et al. (1973). "Release of endotoxin in the form of cell wall blebs during in vitro growth of Neisseria meningitidis," J Exp Med, 138(5):1156-67.

Ellis et al. (2010). "Virulence and immunomodulatory roles of bacterial outer membrane vesicles," Microbiol Mol Biol Rev, 74(1):81-94.

European Office Action dated Feb. 3, 2015, for EP Application No. 11764868, 6 pages.

Experimental data regarding OMV expression following OMV extraction, filed in opposition against EP1534326, dated Oct. 2, 2009, 1 page.

Experimental data: expression of NspA, fHBP and GNA2132 in N. meningitidis, filed in opposition against EP1534326, dated Aug. 4, 2010. 2 pages.

Ferrari et al. (2006). "Outer membrane vesicles from group B Neisseria meningitidis delta gna33 mutant: proteomic and immunological comparison with detergent-derived outer membrane vesicles," Proteomics, 6(6):1856-66.

Frasch et al. (2001). "Outer Membrane Protein Vesicle Vaccines for Meningococcal Disease," Chapter 7 in "Methods in Molecular Medicine, Meningococcal Vaccines: Methods and Protocols," Pollard et al. (Ed), Humana Press, Totowa, New Jersey, vol. 66, pp. 81-107.

Fredrikson et al. (1991). Production, characterization and control of MenB-vaccine "Folkehelsa": an outer membrane vesicle vaccine against group B meningococcal disease. NIPH Annals 14:67-79.

Fukasawa et al. (1999) "Neisseria meningitidis serogroup C polysaccharide and serogroup B outer membrane vesicle conjugate as a bivalent meningococcus vaccine candidate." Vaccine 17:2951-2958.

Fukasawa et al. (2004). "Adjuvant can improve protection induced by OMV vaccine against Neisseria meningitidis serogroups B/C in neonatal mice" FEMS Immunol. Med. Microbiol. 41:205-210.

Fukasawa, Lucila O. et al, Journal of Medical Microbiology, 2003, vol. 52, pp. 121-125, Immune response to native NadA from Neisseria meningitidis and its expression in clinical isoalted in Brazil.

Galeano et al. (1995). "Efectividad de una vacuna antimeningococcica en una cohorte de itagui, Colombia, 1995," Epidemiologico de Antioquia 20(2), 8 pages. (9 page English translation included).

(56) References Cited

OTHER PUBLICATIONS

Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).
Gil et al. (2009). "Proteomic study via a non-gel based approach of meningococcal outer membrane vesicle vaccine obtained from strain CU385," Human Vaccines 5(5):347-356.
Henry, et al.(2004). "Improved methods for producing outer membrane vesicles in Gram-negative bacteria," Research in Microbiology, 155:437-446.
Hoiby et al. (1991). "Bactericidal antibodies after vaccination with the Norwegian meningococcal serogroup B outer membrane vesicle vaccine: a brief survey," NIPH Annals 14(2):147-155.
Hoiby et al. (1991). "The Norwegian meningococcal serogroup B outer membrane vesicle vaccine protection trials: case tracing, meningococcal antigen detection and serological diagnosis," NIPH Annals, 14(2):107-123.
Holst et al. (2003). "Serum bactericidal activity correlates with the vaccine efficacy of outer membrane vesicle vaccines against Neisseria meningitidis serogroup B disease," Vaccine 21(7-8):734-737.
Holst et al. (2009). "Properties and clinical performance of vaccines containing outer membrane vesicles from Neisseria meningitidis," Vaccine; 27 Suppl 2:B3-12.
Interlocutory decision in opposition proceedings, filed in opposition against EP1534326, dated Mar. 25, 2010, 11 pages.
International Preliminary Examination Report dated Aug. 23, 2000, for international patent application No. PCT/US99/11977, filed May 28, 1999, 7 pages.
International Search Report dated Feb. 27, 2012, for PCT/IB2011/053957, 9 pages.
Katial et al. (2002). "Immunogenicity and Safety Testing of a Group B Intranasal Meningococcal Native Outer Membrane Vesicle Vaccine," Infection and Immunity 70(2):702-707.
Koeberling et al. (2007). "Improved immunogenicity of a H44/76 group B outer membrane vesicle vaccine with over-expressed genome-derived Neisserial antigen 1870," Vaccine 25(10):1912-1920.
List of Journals from SpringerProtocols website about Methods in Molecular Biology, filed in Opposition against EP1644035, dated Oct. 18, 2014, 5 pages.
Martin, Patricia et al, Microsatellite instability regulates transcription factor binding and gene expression, PNAS, pp. 3800-3804, Mar. 8, 2005, vol. 102(10).
McLeod et al. (2000). "Structural relationships and sialylation among meningococcal L1, L8, and L3,7 lipooligosaccharide serotypes," J Biol Chem, 275(13):9716-24.
Metruccio, Matteo M.E. et al, PLOS pathogens, Dec. 24, 2009, vol. 5(12), e1000710, pp. 1-13, A Novel Phase Variation Mechanism in the Meningococcus Driven by a Ligand-Responseive repressor and Differential Spacing of Distal Promoter elements.
Metruccio, MME, A novel phase variaion mechanism in the meningococcu driven by a ligand-responsive repressor and differential spacing of distal promoter elements, Bologna 2010, Univeristy of Bologna, pp. 1-84.
Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.
Norheim et al. (2004). "Immunogenicity and bactericidal activity in mice of an outer membrane protein vesicle vaccine against Neisseria meningitidis serogroup a disease," Vaccine, 22: 2171-2180.
Norheim et al. (2005). "Development and characterisation of outer membrane vesicle vaccines against serogroup A Neisseria meningitidis" Vaccine 23(29):3762-3774.
Notice of Allowance, dated Jul. 30, 2015 for U.S. Appl. No. 11/666,786. 9 pages.
Notice of Appeal by Carpmaels & Ransford, filed in Opposition against EP1644035, dated Mar. 24, 2014, 1 page.
Notice of Appeal by GlaxoSmithKline Biologicals S.A., filed in relation to EP1534326, dated Jun. 3, 2010, 2 pages.
Notice of opposition by GlaxoSmithKline Biologicals S.A., filed in opposition against EP1534326, dated Mar. 3, 2008, 19 pages.
Notice of Opposition, filed in Opposition against EP1644035, dated May 24, 2012, 15 pages.
O'Hallahan J, et al. 2004. The strategy to control New Zealand's epidemic of Group B meningococcal disease. PIDJ 23: S293-S298.
Ochoa, Rolando (2008). "Main projects on research, development and manufacturing of human vaccines," excerpt from presentation at BioQatar Symposium 2008, 4 slides.
Office Action dated Nov. 12, 2014 for U.S. Appl. No. 11/666,786. 8 pages.
Oster et al. (2007). "Immunogenicity and safety of a strain-specific MenB OMV vaccine delivered to under 5-year olds in New Zealand," Vaccine, 25:3075-9.
Parkhill et al. (2000). "Complete DNA Sequence of a Serogroup A Strain of Neisseria meningitides Z2491," Nature, 404(6777):502-506.
Patentee's response to Notice of Opposition, filed in Opposition against EP1644035, dated Mar. 12, 2013, 9 pages.
Patentee's response to opposition, filed in opposition against EP1534326, dated Jan. 19, 2009, 11 pages.
Peeters et al. (1996). "Phase I clinical trial with a hexavalent PorA containing meningococcal outer membrane vesicle vaccine," Vaccine 14(10):1009-1015.
Perez et al. (2010). "Community acquired bacterial meningitis in Cuba: a follow up of a decade," BMC Infectious Diseases 10:130, 9 pages.
Perkins et al. (1998). "Immunogenicity of two efficacious outer membrane protein-based serogroup B meningococcal vaccines among young adults in Iceland," *The Journal of Infectious Disease* 177:683-691.
Reply to Statement of Grounds of Appeal by Nederlandsch Octrooibureau, filed in Opposition against EP1644035, dated Oct. 15, 2014, 8 pages.
Rodriguez et al. (1999). "The epidemiological impact of antimeningococal B vaccination in Cuba," Mem Inst Oswaldo Cruz 94(4):433-440.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Rosenqvist et al., "Effect of Aluminum Hydroxide and Meningococcal Serogroup C Capsular Polysaccharide on the Immunogenicity and Reactogenicity of a Group B Neisseria meningitidis Outer Membrane Vesicle Vaccine", Developments in Biological Standardization, vol. 92, pp. 323-333, (1998).
Sacchi et al. (2001). "Serosubtypes and PorA types of Neisseria meningitidis serogroup B isolated in Brazil during 1997-1998: overview and implications for vaccine development," J Clin Microbiol, 39(8):2897-903.
Schielke et al. (May 2009). "Expression of the meningococcal adhesin NadA is controlled by a transcriptional regulator of the MarR family," Molec Microbiol 72(4):1054-1067.
Schielke, S et al, International Journal of Medical Microbiology, vol. 298(suppl. 4-5), p. 81, abstract MPV13, The transcription regulator NadR negatively controls expression of NadA in Neisseria meningitidis, 2008.
Schielke, Stephanie et al, Applied and Environmental Microbiology, May 2010, vol. 76(10), pp. 3160-3169, The transcriptional Repressor FarR is not involved in Meningococcal Fatty Acid Resistance Mediated by the FarAB Efflux Pump and Dependent on Lipopolysaccharide structure.
Schielke, Stephanie et al, International Journal of Medical Microbiology, vol. 301, pp. 325-333, 2001, Characterization of FarR as a highly specialized, growth phase-dependent transcriptional regulator in Neisseria meningitidis.
Serruto et al. (2010). "Neisseria meningitidis GNA2132, a heparin-binding protein that induces protective immunity in humans," PNAS 107(8):3770-3775.
Sierra GV, et al. (1991). Vaccine against group B Neisseria meningitidis: protection trial and mass vaccination results in Cuba. NIPH Ann 14: 195-207.

(56) References Cited

OTHER PUBLICATIONS

Slide printout by Carpmaels & Ransford, filed in opposition against EP1534326, dated Nov. 23, 2009, 2 pages.
Statement of Grounds of Appeal by Carpmaels & Ransford, filed in Opposition against EP1644035, dated May 30, 2014, 5 pages.
Statement of Grounds of Appeal by GlaxoSmithKline Biologicals S.A., filed in relation to EP1534326, dated Aug. 4, 2010, 24 pages.
Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.
Tettelin et al. (Mar. 10, 2000). "Complete Genome Sequence of Neisseria meningitidis Serogroup B Strain MC58," Science 287(5459):1809-1815.
Van de Waterbeemd (2012). "Identification and optimization of critical process parameters for the production of NOMV vaccine against Neisseria meningitidis," Vaccine, 30(24):3683-90.
Van der Ley & Steeghs (2003) "Lessons from an LPS-deficient Neisseria meningitidis mutant" Journal of Endotoxin Research 9(2):124-128.
Van der Ley et al. (1992). "Construction of a Multivalent Meningococcal Vaccine Strain Based on the Class I Outer Membrane Protein," Infection and Immunity 60(8): 3516-3161.
Verheul et al. (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
Vermont et al. (2003). "Meningococcal serogroup B infections: a search for a broadly protective vaccine," Expert Rev Vaccines, 2(5):673-81.
Wedege et al. (2003). "Antibody specificities and effect of meningococcal carriage in Icelandic teenagers receiving the Norwegian serogroup B outer membrane vesicle vaccine," Infect. Immun. 71:3775-3781.
Williams et al., (2007) "Proteomic analysis of outer membranes and vesicles from wild-type serogroup B Neisseria meningitidis and a lipopolysaccharide-deficient mutant" Infection and Immunity 75(3):1364-1372.
Wilson & Walker (Eds.) (1994). "Wilson Principles and techniques of practical biochemistry: Editors: Bryan L. Williams and Keith Wilson," Cambridge University Press, Cambridge, fourth edition, p. 309.
Written submission in preparation to oral proceedings by Carpmaels & Ransford, filed in Opposition against EP1644035, dated Oct. 18, 2013, 2 pages.
Written submission in preparation to oral proceedings by GlaxoSmithKline Biologicals S.A., filed in opposition against EP1534326, dated Sep. 30, 2009, 24 pages.
Written submission in preparation to oral proceedings by Nederlandsch Octrooibureau, filed in Opposition against EP1644035, dated Oct. 18, 2013, 6 pages.
Zollinger et al. (2010). "Design and evaluation in mice of a broadly protective meningococcal group B native outer membrane vesicle vaccine," Vaccine, 28(31):5057-5067.
Boslego et al. (1991). "Gonorrhea Vaccines," Chapter 17 in *Vaccines and Immunotherapy*, Cryz S.J. (Ed.), Pergamon Press: New York, NY, pp. 211-223.
Bowe et al. (Jul. 2004) "Mucosal vaccination against serogroup B meningococci: induction of bacterial antibodies and cellular immunity following intranasal immunization with NadA of Neisseria meningitides and mutants of *Escherichia coli* heat-labile enterotoxin," Infection and Immunity, 72: 4052-4060.
Capecchi et al. (2005) "Neisseria meningitides NadA is a new invasion which promotes bacterial adhesion to and penetration into human epithelial cells," Molecular Microbiology, 55: 687-698.
Comanducci et al. (Jul. 2004) "NadA diversity and carriage in *Neisseria meningitides*," Infection and Immunity, 72: 4217-4223.
Comanducci, M. (2002). "NadA, a Novel Vaccine Candidate of Neisseria Meningitides," Journal of Experimental Medicine 195(11):1445-1454.
Cruse et al. (2003). Illustrated Dictionary of Immunology, $2^{nd}$ Ed. CRC Press, pp. 46, 166, and 382.
Decision revoking EP1534326, filed in Opposition against EP1534326, dated Jan. 15, 2016, 3 pages.
Decision revoking EP1737486, filed in opposition against EP1737486, dated Oct. 28, 2015, 28 pages.
Donnelly et al. (2010). "Qualitative and quantitative assessment of meningococcal antigens to evaluate the potential strain coverage of protein-based vaccines," Proc Natl Acad Sci U S A, 107(45):19490-5.
Gervais et al. (1992). "Putative Lipoprotein Yaec Precursor," Database Swissport Acc No. p28635.
Giuliani et al. (2010). "Measuring antigen-specific bactericidal responses to a multicomponent vaccine against serogroup B meningococcus," Vaccine 28:5023-5030.
Jacobsson et al. (2009). "Prevalence and sequence variations of the genes encoding the five antigens included in the novel 5CVMB vaccine covering group B meningococcal disease" Vaccine. 27:1579-1584.
Legrain et al. (1995). "Production of Lipidated Meningococcal Transferrin Binding Protein 2 in *Escherichia coli*," *Protein Expression and Purification* 6:570-578.
Litt et al. (2004). "Putative vaccine antigens from Neisseria meningitidis recognized by serum antibodies of young children convalescing after meningococcal disease," J Infect Dis 190(8):1488-97.
Lucidarme et al., (2010). "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Magagnoli et al. (2009). "Structural organization of NadADelta(351-405), a recombinant MenB vaccine component, by its physicochemical characterization at drug substance level," Vaccine, 27(15):2156-70.
Martin et al. (1998). "New Zealand epidemic of meningococcal disease identified by a strain with phenotype B:4:P1.4," JID 177:497-500.
Martin et al. (2003). "Experimentally revised repertoire of putative contingency loci in *Neisseria meningitidis* strain MC58: evidence for a novel mechanism of phase variation," Molecular Microbiology 50(1):245-257.
Morley, S. et al. (Dec. 12, 2001). "Vaccine prevention of meningococcal disease, coming soon?" *Vaccine* 20(5-6):666-687.
Novartis (Jun. 9, 2011). "Novartis candidate vaccine Bexsero® shows significant potential in providing broad coverage against meningococcal serogroup B infections." Media Release, 6 pages.
Pizza et al. (2000). "Identification of Vaccine Candidates Against Serogroup B Meningococcus by Whole-Genome Sequencing," Science 287(5459):1816-1820.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Renauld-Mongenie et al. (1997). "Identification of Human Transferrin-Binding Sites Within Meningococcal Transferrin-Binding Protein B," *J. Bacteriology* 197(20):6400-6407.
Seib et al. (2010). "Influence of serogroup B meningococcal vaccine antigens on growth and survival of the meningococcus in vitro and in ex vivo and in vivo models of infection," Vaccine 28(12):2416-2427.
Statement of Grounds of Appeal, filed in relation to EP2353608, dated Jul. 22, 2015, 8 pages.
Tavano et al. (2011). "Mapping of the Neisseria meningitidis NadA cell-binding site: Relevance of predicted $\alpha$-helices in the NH2-terminal and dimeric coiled-coil regions," J Bacteriol 193(1):107-115.
Tramont, (1976) "Specificity of inhibition of epithelial cell adhesion of Neisseria gonorrhoeae." Infection and Immunity 14:593-595.

(56) References Cited

OTHER PUBLICATIONS

Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.

Van der Lay et al. (1995). "Construction of Neisseria Meningitidis Strains Carrying Multiple Chromosomal Copies of the PorA Gene for Use in Production of a Multivalent Outer Membrane Vesicle Vaccine," *Vaccine* 13(4): 401-407.

Voulhoux and Tommassen (2002). "Transport of lipoproteins to the cell surface in Neisseria meningitidis," 13th International Pathogenic Neisseria Conference 2002, p. 31.

Welsch et al. (2002). "Genome-derived antigen (GNA) 2132 elicits protective serum antibodies to groups B and C Neisseria meningitidis strains," 13th International Pathogenic Neisseria Conference 2002, p. 25.

Welsch et al. (2003). "Antibody to genome-derived neisserial antigen 2132, a Neisseria meningitidis candidate vaccine, confers protection against bacteremia in the absence of complement-mediated bactericidal activity" Journal of Infectious Diseases 188 (11):1730-1740.

\* cited by examiner

FIG. 4D

DEVELOPMENTS IN MENINGOCOCCAL OUTER MEMBRANE VESICLES

RELATED APPLICATIONS

This application is a Divisional of U.S. patent application Ser. No. 13/822,238 (now U.S. Pat. No. 9,259,462), which claims an international filing date of Sep. 9, 2011; which is the National Stage of International Application No. PCT/IB2011/053957, filed Sep. 9, 2011; which claims the benefit under 35U.S.C. § 119(e) of U.S. Provisional Patent Application Nos. 61/381,859, filed Sep. 10, 2010; and 61/429,673, filed Jan. 4, 2011, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 303822003801SeqList.txt, date recorded: Dec. 30, 2015, size: 102 KB).

FIELD OF THE INVENTION

This invention is in the field of meningococcal vaccines based on membrane vesicles.

BACKGROUND

Various vaccines against serogroup B of *Neisseria meningitidis* ("MenB") are currently being investigated. Some of these are based on outer membrane vesicles (OMVs), such as the Novartis MENZB™ product, the Finlay Institute VA-MENGOC-BC™ product, and the Norwegian Institute of Public Health MENBVAC™ product. Reference 1 discloses the construction of vesicles from strains modified to express six different PorA subtypes. References 2-4 report pre-clinical studies of an OMV vaccine in which fHbp (also known as GN1870) is over-expressed (and this overexpression can be combined with knockout of LpxL1 [5]). Reference 6 recently reported a clinical study of five formulations of an OMV vaccine in which PorA & FrpB are knocked-out and Hsf & TbpA are over-expressed. Reference 7 reports a native outer membrane vesicle vaccine prepared from bacteria having inactivated synX, lpxL1, and lgtA genes.

It is an object of the invention to provide further and improved meningococcal OMVs, and also to provide further and improved meningococci for use in vaccine production.

DISCLOSURE

A first aspect of the invention provides meningococcal outer membrane vesicles in which NHBA is over-expressed. A second aspect of the invention provides meningococcal outer membrane vesicles in which NadA is over-expressed. A third aspect of the invention provides a panel of bacterial strains, each member of which is isogenic except for a single gene which in each strain encodes a different variant of an antigen of interest.

Over-expression

The first and second aspects of the invention provide meningococcal outer membrane vesicles in which certain antigens are over-expressed. In the first aspect, at least NHBA is over-expressed. In the second aspect, at least NadA is over-expressed. As discussed below, these vesicles are obtained from bacteria which over-express the relevant antigen(s). The bacterium may express the antigen(s) already, but include a genetic modification which, compared to a bacterium without that modification, increases expression of the antigen. This modification will usually be introduced using recombinant techniques, such as site-directed mutagenesis or targeted homologous recombination, so vesicles of the invention are usually obtained from recombinant bacteria. Typically a bacterium will include (i) a gene under the control of a promoter with which it is not found in nature and/or (ii) a knockout of a gene which is found in the bacterium in nature.

As a result of the over-expression, outer membrane vesicles prepared from the modified meningococcus contain higher levels of the over-expressed antigen(s). The increase in expression in the OMVs is usefully at least 10%, measured in mass of the relevant antigen per unit mass of OMV, and is more usefully at least 20%, 30%t 40%, 50%, 75%, 100% or more.

Suitable recombinant modifications which can be used to cause over-expression of an antigen include, but are not limited to: (i) promoter replacement; (ii) gene addition; (iii) gene replacement; or (iv) repressor knockout.

In promoter replacement, the promoter which controls expression of the antigen's gene in a bacterium is replaced with a promoter which provides higher levels of expression. For instance, the gene might be placed under the control of a promoter from a housekeeping metabolic gene. In other embodiments, the antigen's gene is placed under the control of a constitutive or inducible promoter. Similarly, the gene can be modified to ensure that its expression is not subject to phase variation. Methods for reducing or eliminating phase variability of gene expression in meningococcus are disclosed in reference 8. These methods include promoter replacement, or the removal or replacement of a DNA motif which is responsible for a gene's phase variability.

In gene addition, a bacterium which already expresses the antigen receives a second copy of the relevant gene. This second copy can be integrated into the bacterial chromosome or can be on an episomal element such as a plasmid. The second copy can have a stronger promoter than the existing copy. The gene can be placed under the control of a constitutive or inducible promoter. The effect of the gene addition is to increase the amount of expressed antigen. Where a plasmid is used, it is ideally a plasmid with a high copy number e.g. above 10, or even above 100.

In gene replacement, gene addition occurs but is accompanied by deletion of the existing copy of the gene. For instance, this approach was used in reference 4, where a bacterium's endogenous chromosomal fHbp gene was deleted and replaced by a plasmid-encoded copy (see also reference 9). Expression from the replacement copy is higher than from the previous copy, thus leading to over-expression.

In repressor knockout, a protein which represses expression of an antigen of interest is knocked out. Thus the repression does not occur and the antigen of interest can be expressed at a higher level.

Promoters for over-expressed genes can advantageously include a CREN [10].

A over-expressing modified strain will generally be isogenic with its parent strain, except for a genetic modification. As a result of the modification, expression of the antigen of interest in the modified strain is higher (under the same conditions) than in the parent strain. A typical modification will be to place a gene under the control of a promoter with which it is not found in nature and/or to knockout a gene which encodes a repressor.

In embodiments where NHBA is over-expressed, various approaches can be used. For convenience, the approach already reported in reference 11 can be used i.e. introduction of a NHBA gene under the control of an IPTG-inducible promoter. By this approach the level of expression of NHBA can be proportional to the concentration of IPTG added to a culture. The promoter may include a CREN.

In embodiments where NadA is over-expressed, various approaches can be used. One useful approach involves deletion of the gene encoding NadR (NMB1843), which is a transcriptional repressor protein [12] which down-regulates or represses the NadA-encoding gene in all strains tested. Knockout of NadR results in high-level constitutive expression of NadA. An alternative approach to achieve NadA over-expression is to add 4-hydroxyphenylacetic to the culture medium. A further approach is to introduce a NadA gene under the control of an IPTG-inducible promoter.

In some embodiments a bacterium over-expresses both NHBA and NadA.

In addition to over-expressing NHBA and/or NadA, a bacterium may over-express one or more further antigens. For instance, a bacterium may over-express one or more of: (a) NhhA; (b) TbpA; (c) HmbR; (d) TbpB; (e) NspA; (f) Cu,Zn-superoxide dismutase; (g) Omp85; (h) App; and/or (i) fHbp. Over-expression of NhhA is already reported in references 6 and 13. Over-expression of TbpA is already reported in references 6, 13 and 14. Over-expression of HmbR is already reported in reference 15. Over-expression of TbpB is already reported in reference 14. Over-expression of NspA is already reported in reference 16, in combination with porA and cps knockout. Over-expression of Cu,Zn-superoxide dismutase is already reported in reference 14. Over-expression of fHbp is already reported in references 2-4 & 9, and by a different approach (expressing a constitutively-active mutant FNR) in references 17 & 18.

In some embodiments a bacterium over-expresses NHBA, NadA and fHbp. These three antigens are components of the "universal vaccine" disclosed in reference 19 or "4CMenB" [20,21]. In one embodiment, expression of NHBA is controlled by a strong promoter, NadR is knocked out and the strain expresses a constitutively active mutant FNR. In another embodiment, expression of NHBA is controlled by a strong promoter, expression of fHbp is controlled by a strong promoter, and NadR is knocked out. The bacterium can also be a bacterium which does not express an active MltA (GNA33), such that it spontaneously releases vesicles which contain NHBA, NadA and fHbp. Ideally, the bacterium does not express a native LPS e.g. it has a mutant or knockout of LpxL1.

Vesicles

The first and second aspects of the invention provide meningococcal outer membrane vesicles. These outer membrane vesicles include any proteoliposomic vesicle obtained by disruption of or blebbling from a meningococcal outer membrane to form vesicles therefrom that retain antigens from the outer membrane. Thus the term includes, for instance, OMVs (sometimes referred to as 'blebs'), microvesicles (MVs [22]) and 'native OMVs' ('NOMVs' [23]).

MVs and NOMVs are naturally-occurring membrane vesicles that form spontaneously during bacterial growth and are released into culture medium. MVs can be obtained by culturing Neisseria in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 24 & 25 describe Neisseria with high MV production.

OMVs are prepared artificially from bacteria, and may be prepared using detergent treatment (e.g. with deoxycholate), or by non-detergent means (e.g. see reference 26). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [27 & 28] being preferred for treating Neisseria) at a pH sufficiently high not to precipitate the detergent [29]. Other techniques may be performed substantially in the absence of detergent [26] using techniques such as sonication, homogenisation, microfluidisation, cavitation, osmotic shock, grinding, French press, blending, etc. Methods using no or low detergent can retain useful antigens such as NspA [26]. Thus a method may use an OMV extraction buffer with about 0.5% deoxycholate or lower e.g. about 0.2%, about 0.1 %, <0.05% or zero.

A useful process for OMV preparation is described in reference 30 and involves ultrafiltration on crude OMVs, rather than instead of high speed centrifugation. The process may involve a step of ultracentrifugation after the ultrafiltration takes place.

Another useful process for outer membrane vesicle production is to inactivate the mltA gene in a meningococcus, as disclosed in reference 31. These mutant bacteria spontaneously release vesicles into their culture medium.

If lipo-oligosaccharide (LOS) is present in a vesicle it is possible to treat the vesicle so as to link its LOS and protein components ("infra-bleb" conjugation [43]).

The vesicles may lack LOS altogether, or they may lack hexa-acylated LOS e.g. LOS in the vesicles may have a reduced number of secondary acyl chains per LOS molecule [32]. For example, the vesicles may from a strain which has a lpxL1 deletion or mutation which results in production of a penta-acylated LOS [3,7]. LOS in a strain may lack a lacto-N-neotetraose epitope e.g. it may be a 1st and/or lgtB knockout strain [6], LOS may lack at least one wild-type primary O-linked fatty acid [33]. LOS having. The LOS may have no α chain. The LOS may comprise GlcNAc-$Hep_2$phosphoethanolamine-$KDO_2$-Lipid A [34].

The vesicles may include one, more than one, or (preferably) zero PorA serosubtypes. Modification of meningococcus to provide multi-PorA OMVs is known e.g. from references 1 and 35. Conversely, modification to remove PorA is also known e.g. from reference 6.

The vesicles may be free from one of both of PorA and FrpB. Preferred vesicles are PorA-free.

The invention may be used with mixtures of vesicles from different strains. For instance, reference 36 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. Reference 37 also discloses useful combinations of different vesicles. A combination of vesicles from strains in each of the L2 and L3 immunotypes may be used in some embodiments.

Bacteria

As mentioned above, OMVs of the invention ate prepared from meningococci which over-express the relevant antigen(s) due to genetic modification. The invention also provides these bacteria. The bacteria can be used for preparing OMVs of the invention.

In addition to genetic modification(s) which cause over-expression of the antigen(s) of interest, the bacteria may include one or more further modifications. For instance, the bacterium may have a knockout of one or more of lpxL1, lgtB, porA, frpB, synX, lgtA, mltA and/or lst.

The bacterium may have low endotoxin levels, achieved by knockout of enzymes involved in LPS biosynthesis [38,39].

The bacterium may be from any serogroup e.g. A, B, C, W135, Y. It is preferably serogroup B.

The bacterium may be of any serotype (e.g. 1, 2a, 2b, 4, 14, 15, 16, etc.), any serosubtype, and any immunotype (e.g. L1; L2; L3; L3,3,7; L10; etc.). Vesicles can usefully be prepared from strains having one of the following subtypes: P1.2; P1.2,5; P1.4; P1.5; P1.5,2; P1.5.c; P1.5c,10; P1.7,16; P1.7,16b; P1.7h,4; P1.9; P1.15; P1.9,15; P1.12,13; P1.13; P1.14; P1.21,16; P1.22,14.

The bacterium may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 40] e.g. the ET-37 complex is the ST-11 complex by MLST, the ET-5 complex is ST-32 (ET-5), lineage 3 is ST-41/44, etc.

In some embodiments a bacterium may include one or more of the knockout and/or hyper-expression mutations disclosed in references 16 and 41-43. Suitable genes for modification include: (a) Cps, CtrA, CtrB, CtrC, CtrD, FrpB, GalE, HtrB/MsbB, LbpA, LbpB, LpxK, Opa, Opc, PilC PorB, SiaA, SiaB, SiaC, SiaD, TbpA, and/or TbpB [41]; (b) CtrA, CtrB, CtrC, CtrD, FrpB, GalE, HtrB/MsbB, LbpA, LbpB, LpxK, Opa, Opc, PhoP, PilC, PmrE, PmrE, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; and (d) CtrA, CtrB, CtrD, FrpB, OpA, OpC, PilC, PorB, SiaD, SynA, SynB, and/or SynC.

A bacterium may have one or more, or all, of the following characteristics: (i) down-regulated or knocked-out LgtB and/or GalE to truncate the meningococcal LOS: (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex, A truncated LOS can be one that does not include a sialyl-lacto-N-neotetraose epitope e.g. it might be a galactose-deficient LOS. The LOS may have no α chain.

Strain Production

The invention provides a process for preparing a meningococcal strain suitable for OMV preparation, comprising steps of (i) choosing a starting strain which expresses a first amount of an antigen when grown in specific culture conditions, then (ii) modifying the starting strain to provide a modified strain, wherein the modified strain expresses a second amount of the antigen when grown in the same specific culture conditions, wherein the second amount is higher than the first amount; wherein the antigen is either NHBA or NadA, The second amount of NHBA or NadA is usefully at least 10%, higher than the first amount, measured in mass of the relevant antigen per unit mass of bacteria, and is more usefully at least 20%, 30%, 40%, 50%, 75%, 100% or more.

The invention provides a process for preparing a meningococcal strain suitable for OMV preparation, comprising steps of (i) choosing a starting strain which expresses NHBA and/or NadA; and (ii) modifying the starting strain to increase the amount of NHBA and/or NadA which it expresses. The increased amount after modification in step (ii) is usefully at least 10%, higher than the first amount, measured in mass of the relevant antigen per unit mass of bacteria, and is more usefully at least 20%, 30%, 40%, 50%, 75%, 100% or more.

Either of these processes can be followed by a step of (iii) culturing the modified bacteria obtained in step (ii) to provide a bacterial culture.

In step (ii), the modification to increase expression of NHBA and/or NadA can be any of the modifications discussed above. For instance, the strain can be modified by knocking out expression of NadR, thereby increasing expression of NadA. The strain can also be modified to increase or decrease expression of other polypeptides, as described elsewhere herein e.g. to increase its fHbp expression, such as by introducing a gene which encodes a constitutively-active mutant FNR.

The invention also provides a process for preparing a meningococcal vesicle, comprising a step of treating a bacterial culture obtained by a process of the invention (as described above) such that its outer membrane forms vesicles. This treatment step can use any of the techniques discussed above.

The invention also provides a process for preparing a meningococcal vesicle, comprising a step of treating a meningococcus of the invention such that its outer membrane forms vesicles. This treatment step can use any of the techniques discussed above.

Useful starting strains are in meningococcus serogroup B. Four useful starting meningococcal strains for preparing bacteria which over-express an antigen of interest are MC58, NZ05/33, H44/76 and GB013. MC58 has PorA serosubtype 1.7,16; NZ05/33 has serosubtype 1.7-2,4; H44/76 has serosubtype 1.7,16; and GB013 has serosubtype 1.22,9.

Iogenic Panels

A third aspect of the invention provides a panel of bacterial strains (e.g. meningococci), each member of which is isogenic except for a single gene which in each strain encodes a different variant of an antigen of interest. Thus the only genetic difference between each member of the panel is the coding sequence for this antigen. This panel can be used to study the immunological effect of polymorphic forms of a gene of interest found in different wild-type strains, without having to worry about variability due to differences in those strains which are unrelated to the antigen of interest. For instance, these panels can be used as test strains in a scrum bactericidal antibody assay to provide a constant genetic background for assessing the cross-population killing of bacteria by antibodies which were raised against a specific sequence variant.

A useful panel for an antigen of interest can be made be selecting a starting strain of meningococcus. A useful starting strain does not express the antigen of interest; if the starting strain does express the antigen of interest then expression of the endogenous gene can be knocked out e.g. by insertion of a marker gene. To create a panel, a site in the bacterial genome is chosen for insertion of a gene encoding the antigen of interest. This site can be under the control of a promoter, such that different coding sequences can be introduced for expression from this promoter, or it can lack a promoter, in which case the introduced sequences should include a promoter. An important feature of the panel is that each member has the same promoter for expression of the antigen of interest, in the same location in the genome, such that the only genetic difference between them is the coding sequence for the antigen of interest.

The antigen of interest, which differs between panel members, can be any useful antigen which exists in polymorphic forms across a bacterial population. Thus, for meningococcus, the antigen of interest could be e.g. fHbp, NadA, NHBA, Omp85, HmbR, NhhA, App, NspA, TbpA. etc.

The general approach of creating an isogenic panel for testing the effect of sequence variability is not restricted to meningococcus and can be used for any other bacterium.

Antigens

NHBA (Neisserial Heparin Binding Antigen)

NHBA [11] was included in the published genome sequence for meningococcal serogroup B strain MC58 [68] as gene NMB2132 (GenBank accession number GI:7227388; SEQ ID NO: 9 herein). Sequences of NHBA from many strains have been published since then. For example, allelic forms of NHBA (referred to as protein '287') can be seen in FIGS. 5 and 15 of reference 44, and in example 13 and FIG. 21 of reference 45 (SEQ IDs 3179 to 3184 therein). Various immunogenic fragments of NHBA have also been reported.

Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14,16, 18, 20, 25, 30, 35, 40, 50, 60, 70, 80, 90, 100, 150, 200, 250 or more). Preferred fragments of (b) comprise an epitope from SEQ ID NO: 9.

The most useful NHBA antigens can elicit antibodies which, after administration to a subject, can bind to a meningococcal polypeptide consisting of amino acid sequence SEQ ID NO: 9. Advantageous NHBA antigens for use with the invention can elicit bactericidal anti-meningococcal antibodies after administration to a subject.

NadA (Neisserial Adhesin A)

The NadA antigen was included in the published genome sequence for meningococcal serogroup B strain MC58 [68] as gene NMB1994 (GenBank accession number GI:7227256; SEQ ID NO: 10 herein). The sequences of NadA antigen from many strains have been published since then, and the protein's activity as a Neisserial adhesion has been well documented. Various immunogenic fragments of NadA have also been reported.

Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10.

The most useful NadA antigens can elicit antibodies which, after administration to a subject, can bind to a meningococcal polypeptide consisting of amino acid sequence SEQ ID NO: 10. Advantageous NadA antigens for use with the invention can elicit bactericidal anti-meningococcal antibodies after administration to a subject. SEQ ID NO: 6 is one such fragment.

HmbR

The full-length HmbR sequence was included in the published genome sequence for meningococcal serogroup B strain MC58 [68] as gene NMB1668 (SEQ ID NO: 7 herein). Reference 46 reports a HmbR sequence from a different strain (SEQ ID NO: 8 herein), and reference 15 reports a further sequence (SEQ ID NO: 19 herein). SEQ ID NOs: 7 and 8 differ in length by 1 amino acid and have 94.2% identity. SEQ ID NO: 19 is one amino acid shorter titan SEQ ID NO; 7 and they have 99% identity (one insertion, seven differences) by CLUSTALW. The invention can use any such HmbR polypeptide.

The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 7, where the value of i is 50, 60, 70, 80, 90, 95, 99 or more. In other embodiments a HmbR sequence used according to the invention may comprise a fragment of at least j consecutive amino acids from SEQ ID NO: 7, where the value of j is 7, 8, 10, 12,14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 7 and/or (ii) comprising a fragment of at least j consecutive amino acids from SEQ ID NO: 7.

Preferred fragments of j amino acids comprise an epitope from SEQ ID NO: 7. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 47. Fragments that retain a transmembrane sequence are useful, because they can be displayed on the bacterial surface e.g. in vesicles. Examples of long fragments of HmbR correspond to SEQ ID NOs: 21 and 22. If soluble HmbR is used, however, sequences omitting the transmembrane sequence, but typically retaining epitope(s) from the extracellular portion, can be used.

The most useful HmbR antigens can elicit antibodies which, after administration to a subject, can bind to a meningococcal polypeptide consisting of amino acid sequence SEQ ID NO: 7. Advantageous HmbR antigens for use with the invention can elicit bactericidal anti-meningococcal antibodies after administration to a subject.

fHbp (Factor H Binding Protein)

The fHbp antigen has been characterised in detail. It has also been known as protein '741' [SEQ IDs 2535 & 2536 in ref. 45], 'NMB1870', 'GNA1870' [refs. 48-50], 'P2086', 'LP2086' or 'ORF2086' [51-53]. It is naturally a lipoprotein and is expressed across all meningococcal serogroups. The structure of fHbp's C-terminal immunodominant domain ('fHbpC') has been determined by NMR [54]. This part of the protein forms an eight-stranded β-barrel, whose strands are connected by loops of variable lengths. The barrel is preceded by a short α-helix and by a flexible N-terminal tail.

The fHbp antigen falls into three distinct variants [55] and it has been found that serum raised against a given family is bactericidal within the same family, but is not active against strains which express one of the other two families i.e. there is intra-family cross-protection, but not inter-family cross-protection. The invention can use a single fHbp variant, but is will usefully include a fHbp from two or three of the variants. Thus it may use a combination of two or three different fHbps, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least 2 contiguous amino acids from SEQ ID NO: 3.

The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92,93, 94, 95, 96, 97, 98, 99, 99.5, or more. The value of c is at least 85 e.g. 86, 87, 88, 89, 90, 91, 92, 93, 94, 95, 96, 97, 98,99, 99.5, or more. The values of a, b and c are not intrinsically related to each other.

The value of x is at least 7 e.g. 8, 9, 10, 11, 12, 13, 14, 15,16, 17, 18, 19, 20, 21,22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

Where the invention uses a single fHbp variant, a composition may include a polypeptide comprising (a) an amino acid sequence having at least a % sequence identity to SEQ ID NO: 1 and/or comprising an amino acid sequence consisting of a fragment of at least x contiguous amino acids from SEQ ID NO: 1; or (b) an amino acid sequence having at least b % sequence identity to SEQ ID NO: 2 and/or comprising an amino acid sequence consisting of a fragment of at least y contiguous amino acids from SEQ ID NO: 2; or (c) an amino acid sequence having at least c % sequence identity to SEQ ID NO: 3 and/or comprising an amino acid sequence consisting of a fragment of at least z contiguous amino acids from SEQ ID NO: 3.

Where the invention uses a fHbp from two or three of the variants, a composition may include a combination of two or three different fHbps selected from: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third polypeptide, comprising an amino acid sequence having at least c % sequence identity to SEQ ID NO: 3 and/or comprising an amino acid sequence consisting of a fragment of at least z contiguous amino acids from SEQ ID NO: 3. The first, second and third polypeptides have different amino acid sequences.

Where the invention uses a fHbp from two of the variants, a composition can include both: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; and (b) a second polypeptide, comprising an amino acid sequence having at least b % sequence identity to SEQ ID NO: 2 and/or comprising an amino acid sequence consisting of a fragment of at least y contiguous amino acids from SEQ ID NO: 2. The first and second polypeptides have different amino acid sequences.

Where the invention uses a fHbp from two of the variants, a composition can include both: (a) a first polypeptide, comprising an amino acid sequence having at least a % sequence identity to SEQ ID NO: 1 and/or comprising an amino acid sequence consisting of a fragment of at least x contiguous amino acids from SEQ ID NO: 1; (b) a second polypeptide, comprising an amino acid sequence having at least c % sequence identity to SEQ ID NO: 3 and/or comprising an amino acid sequence consisting of a fragment of at least z contiguous amino acids from SEQ ID NO: 3. The first and second polypeptides have different amino acid sequences.

Another useful fHbp which can be used according to the invention is one of the modified forms disclosed, for example, in reference 56 comprising SEQ ID NO: 20 or 23 therefrom. These modified forms can elicit antibody responses which are broadly bactericidal against meningococci.

fHbp protein(S) in a OMV will usually be lipidated at a N-terminus cysteine. In other embodiments they will not be lipidated.

NspA (Neisserial Surface Protein A)

The NspA antigen was included in the published genome sequence for meningococcal serogroup B strain MC58 [68] as gene NMB0663 (GenBank accession number GI:7225888; SEQ ID NO: 11 herein). The antigen was previously known from references 57 & 58. The sequences of NspA antigen from many strains have been published since then. Various immunogenic fragments of NspA have also been reported.

Preferred NspA antigens for use with the invention comprise un amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11.

The most useful NspA antigens can elicit antibodies which, after administration to a subject, can bind to a meningococcal polypeptide consisting of amino acid sequence SEQ ID NO: 11. Advantageous NspA antigens for use with the invention can elicit bactericidal anti-meningococcal antibodies after administration to a subject.

NhhA (*Neisseria* Hia Homologate)

The NhhA antigen was included in the published genome sequence for meningococcal serogroup B strain MC58 [68] as gene NMB0992 (GenBank accession number GI:7226232; SEQ ID NO: 12 herein). The sequences of NhhA antigen front many strains have been published since e.g. refs 44 & 59, and various immunogenic fragments of NhhA have been reported. It is also known as Hsf.

Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12.

The most useful NhhA antigens can elicit antibodies which, after administration to a subject, can bind to a meningococcal polypeptide consisting of amino acid sequence SEQ ID NO: 12. Advantageous NhhA antigens for use with the invention can elicit bactericidal anti-meningococcal antibodies after administration to a subject.

App (Adhesion and Penetration Protein)

The App antigen was included in the published genome sequence for meningococcal serogroup B strain MC58 [68] as gene NMB1985 (GenBank accession number GI:7227246; SEQ ID NO: 13 herein). The sequences of App antigen from many strains have been published since then. It has also been known as 'ORF1' and 'Hap'. Various immunogenic fragments of App have also been reported.

Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13.

The most useful App antigens can elicit antibodies which, after administration to a subject, can bind to a meningococcal polypeptide consisting of amino acid sequence SEQ ID NO: 13. Advantageous App antigens for use with the invention can elicit bactericidal anti-meningococcal antibodies after administration to a subject.

Omp 85 (85 kDa Outer Membrane Protein)

The Omp85 antigen was included in the published genome sequence for meningococcal serogroup B strain MC58 [68] as gene NMB0182 (GenBank accession number GI:7225401; SEQ ID NO: 14 herein). The sequences of Omp85 antigen from many strains have been published since then. Further information on Omp85 can be found in references 60 and 61. Various immunogenic fragments of Omp85 have also been reported.

Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 14.

The most useful Omp85 antigens can elicit antibodies which, after administration to a subject, can bind to a meningococcal polypeptide consisting of amino acid sequence SEQ ID NO: 14. Advantageous Omp85 antigens for use with the invention can elicit bactericidal anti-meningococcal antibodies after administration to a subject.

TbpA

The TbpA antigen was included in the published genome sequence for meningococcal serogroup 8 strain MC58 [68] as gene NMB0461 (GenBank accession number GI:7225687; SEQ ID NO: 23 herein). The sequences of TbpA from many strains have been published since then. Various immunogenic fragments of TbpA have also been reported.

Preferred TbpA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 23.

The most useful TbpA antigens can elicit antibodies which, after administration to a subject, can bind to a meningococcal polypeptide consisting of amino acid sequence SEQ ID NO: 23. Advantageous TbpA antigens for use with the invention can elicit bactericidal anti-meningococcal antibodies after administration to a subject.

TbpB

The TbpB antigen was included in the published genome sequence for meningococcal serogroup B strain MC58 [68] as gene NMB1398 (GenBank accession number GI:7225686; SEQ ID NO: 24 herein). The sequences of TbpB from many strains have been published since then. Various immunogenic fragments of TbpB have also been reported.

Preferred TbpB antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 24.

The most useful TbpB antigens can elicit antibodies which, after administration to a subject, can bind to a meningococcal polypeptide consisting of amino acid sequence SEQ ID NO: 24. Advantageous TbpB antigens for use with the invention can elicit bactericidal anti-meningococcal antibodies after administration to a subject.

Cu,Zn-Superoxide Dismutase

The Cu,Zn-superoxide dismutase antigen was included in the published genome sequence for meningococcal serogroup B strain MC58 [68] as gene NMB1398 (GenBank accession number GI:7226637; SEQ ID NO: 25 herein). The sequences of Cu,Zn-superoxide dismutase from many strains have been published since then. Various immunogenic fragments of Cu,Zn-superoxide dismutase have also been reported.

Preferred Cu,Zn-superoxide dismutase antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 25.

The most useful Cu,Zn-superoxide dismutase antigens can elicit antibodies which, after administration to a subject, can bind to a meningococcal polypeptide consisting of amino acid sequence SEQ ID NO: 25. Advantageous Cu,Zn-superoxide dismutase antigens for use with the invention can elicit bactericidal anti-meningococcal antibodies after administration to a subject.

Pharmaceutical Compositions

Vesicles of the invention are useful as active ingredients in immunogenic pharmaceutical compositions for administration to a patient. These will typically include a pharmaceutically acceptable carrier, and a thorough discussion of such carriers is available in reference 62.

Effective dosage volumes can be routinely established, but a typical human dose of the composition has a volume of about 0.5 ml e.g. for intramuscular injection. The RIVM OMV-based vaccine was administered in a 0.5 ml volume [63] by intramuscular injection to the thigh or upper arm. MeNZB™ is administered in a 0.5 ml by intramuscular injection to the anterolateral thigh or the deltoid region of the arm. Similar doses may be used for other delivery routes e.g. an intranasal OMV-based vaccine for atomisation may have a volume of about 100 μor about 130 μper spray, with four sprays administered to give a total dose of about 0.5 ml.

The pH of a composition of the invention is usually between 6 and 8, and more preferably between 6.5 and 7.5 (e.g. about 7). The pH of the RIVM OMV-based vaccine is 7.4 [64], and a pH<7.5 is preferred for compositions of the invention. The RIVM OMV-based vaccine maintains pH by using a 10 mM Tris/HCl buffer, and stable pH in compositions of the invention may be maintained by the use of a buffer e.g. a Tris buffer, a citrate buffer, phosphate buffer, or a histidine buffer. Thus compositions of the invention will generally include a buffer.

The composition may be sterile and/or pyrogen-free. Compositions of the invention may be isotonic with respect to humans.

Compositions of the invention for administration to patients are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. A dose of about 0.9 mg protein per ml is typical for OMV-based intranasal vaccines.

Compositions of the invention may include an immunological adjuvant. Thus, for example, they may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref. 65), or mixtures thereof. The stilts can take any suitable form (e.g. gel, crystalline, amorphous, etc.). with adsorption of antigen to the salt being preferred. The concentration of $Al^{+++}$ in a composition for administration to a patient is preferably less than 5 mg/ml e.g. ≤4 mg/ml, ≤3 mg/ml, ≤2 mg/ml, ≤1 mg/ml, etc. A preferred range is between 0.3 and 1 mg/ml. A maximum of 0.85 mg/dose is preferred. Aluminium hydroxide adjuvants are particularly suitable for use with meningococcal vaccines.

Meningococci affect various areas of the body and so the compositions of the invention may be prepared in various liquid forms. For example, the compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a Tween (polysorbate), such as Tween 80. Detergents ate generally present at low levels e.g. <0.01%.

Compositions of the invention may include residual detergent (e.g. deoxycholate) from OMV preparation. The amount of residual detergent is preferably less than 0.4 μg (more preferably less than 0.2 μg) for every μg of MenB protein.

If a composition of the invention includes LOS, the amount of LOS is preferably less than 0.12 μg (more preferably less than 0.05 μg) for every μg of protein.

Compositions of the invention may include sodium salts (e.g. sodium chloride) to give tonicity. A concentration of 10±2 mg/ml NaCl is typical e.g. about 9 mg/ml.

Methods of Treatment

The invention also provides a method for raising an immune response in a mammal, comprising administering a composition of the invention to the mammal. The immune response is preferably protective and preferably involves antibodies. The method may raise a booster response in a patient that has already been primed against *N.meningitidis*.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides vesicles of the invention for use as a medicament. The medicament is preferably used to raise an immune response in a mammal (i.e. it is an immunogenic composition) and is more preferably a vaccine.

The invention also provides the use of vesicles of the invention in the manufacture of a medicament for raising an immune response in a mammal.

These uses and methods are preferably for the prevention and/or treatment of a disease caused by *N.meningitidis* e.g. bacterial (or, more specifically, meningococcal) meningitis, or septicemia.

One way of checking efficacy of therapeutic treatment involves monitoring Neisserial infection after administration of the composition of the invention. One way of checking efficacy of prophylactic treatment involves monitoring immune responses against antigens after administration of the composition. Immunogenicity of compositions of the invention can be determined by administering them to test subjects (e.g. children 12-16 months age, or animal models [66]) then determining standard parameters including serum bactericidal antibodies (SBA) and ELISA liters (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

In general, compositions of the invention are able to induce serum bactericidal antibody responses after being administered to a subject. These responses are conveniently measured in mice and are a standard indicator of vaccine efficacy. Serum bactericidal activity (SBA) measures bacterial killing mediated by complement, and can be assayed using human or baby rabbit complement. WHO standards require a vaccine to induce at least a 4-fold rise in SBA in more than 90% of recipients. MeNZB™ elicits a 4-fold rise in SBA 4-6 weeks after administration of the third dose.

Preferred compositions can confer an antibody titre in a human subject patient that is superior to the criterion for seroprotection for an acceptable percentage of subjects. Antigens with an associated antibody titre above which a host is considered to be seroconverted against the antigen are well known, and such liters are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by any other suitable route. The invention may be used to elicit systemic and/or mucosal immunity. Intramuscular administration to the thigh or the upper arm is preferred, injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. The OMV-based RIVM vaccine was tested using a 3- or 4-dose primary schedule, with vaccination at 0, 2 & 8 or 0, 1, 2 & 8 months. MeNZB™ is administered sis three doses at six week intervals.

Compositions of the invention may be used to induce bactericidal antibody responses against more than one hypervirulent lineage of meningococcus. In particular, they can preferably induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-I or ET-37 complex, and against other lineages e.g. hyperinvasive lineages. This does not necessarily mean that the composition can induce bactericidal antibodies against each and every strain of meningococcus within these hypervirulent lineages e.g. rather, for any given group of four of more strains of meningococcus within a particular hypervirulent lineage, the antibodies induced by the composition ate bactericidal against at least 50% (e.g. 60%, 70%, 80%, 90% or more) of die group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}, 2^{11}, 2^{12}, 2^{13}, 2^{14}, 2^{15}, 2^{16}, 2^{17}, 2^{18}$ or higher, preferably at least $2^{14}$) e.g. the serum is able to kill at least 50% of test bacteria of a particular strain when diluted 1/1024.

Useful compositions can induce bactericidal responses against the following strains of serogroup B meningococcus: (i) from cluster A4, strain 961-5945 (B:2b:P1.21,16) and/or strain G2136 (B:−); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:−). More preferred compositions can induce bactericidal responses against strains 961-5945, 44/76 and 394/98.

Strains 961-5945 and G2136 are both *Neisseria* MLST reference strains [ids 638 & 1002 in ref. 67]. Strain MC58 is widely available (e.g. ATCC BAA-335) and was the strain sequenced in reference 68. Strain 44/76 has been widely used and characterised (e.g. ref. 69) and is one of the *Neisseria* MLST reference strains [id 237 in ref. 67; row 32 of Table 2 in ref. 40]. Strain 394/98 was originally isolated in New Zealand in 1998. and there have been several published studies using this strain (e.g. refs. 70 & 71). Strain BZ198 is another MLST reference strain (id 409 in ref. 67; row 41 of Table 2 in ref. 40).

Further Antigenic Components

In addition to vesicles of the invention, an immunogenic composition can include further antigens.

In some embodiments, a composition includes one or more capsular saccharides from meningococci e.g. from serogroups A, C, W135 and/or Y. These saccharides will usually be conjugated to a protein carrier. A composition of the invention may include one or more conjugates of capsular saccharides from 1, 2, 3, or 4 of meningococcal serogroups A, C, W135 and Y e.g. A+C, A+W135, A+Y, C+W135, C+Y, W135+Y, A+C+W135, A+C+Y, A+W135+Y, A+C+W135+Y, etc. Components including saccharides from all four of serogroups A, C, W135 and Y are ideal.

As well as containing antigens from *N.meningitidis*, compositions may include antigens from further pathogens. For example, the composition may comprise one or more of the following further antigens:

an antigen from *Streptococcus pneumoniae*, such as a saccharide (typically conjugated)
  an antigen from hepatitis B virus, such as the surface antigen HBsAg.
  an antigen from *Bordetella pertussis*, such as pertussis holotoxin (PT) and filamentous hemagglutinin (FHA) from *B.pertussis*, optionally also in combination with pertactin and/or agglutinogens 2 and 3.
  a diphtheria antigen, such as a diphtheria toxoid.
  a tetanus antigen, such as a tetanus toxoid.
  a saccharide antigen from *Haemophilus influenzae* B (Hib), typically conjugated.
  inactivated poliovirus antigens.

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

If a Hib saccharide is included (typically as a conjugate), the saccharide moiety may be a polysaccharide (e.g. full-length polyribosylribitol phosphate (PRP) as purified from bacteria), but it is also possible to fragment the purified saccharide to make oligosaccharides (e.g. MW from ~1 to ~5 kDa) e.g. by hydrolysis. The concentration of Hib conjugate in a composition will usually be in the range of 0.5 µg to 50 µg e.g. from 1-20 µg, from 10-15 µg, from 12-16 µg, etc. The amount may be about 15 g, or about 12.5 µg in some embodiments. A mass of less than 5 µg may be suitable [72] e.g. in the range 1-5 µg, 2-4 µg, or about 2.5 µg. As described above, in combinations that include Hib saccharide and meningococcal saccharides, the dose of the former may be selected based on the dose of the latter (in particular, with multiple meningococcal serogroups, their mean mass). Further characteristics of Hib conjugates are as disclosed above for meningococcal conjugates, including choice of carrier protein (e.g. CRM 197 or tetanus toxoid), linkages, ratios, etc.

If a *S.pneumoniae* antigen is included, this may be a polypeptide or a saccharide. Conjugates capsular saccharides are particularly useful for immunising against pneumococcus. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides arc presented as intact polysaccharides while one (the 18C serotype) is presented as an oligosaccharide. A composition may include a capsular saccharide from one or more of the following pneumococcal serotypes: 1, 2, 3, 4, 5, 6A, 6B, 7F, 8, 9N, 9V, 10A, 11A, 12F, 14, 15B, 17F, 18C, 19A, 19F, 20, 22F, 23F and/or 33F. A composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F, etc. Further characteristics of pneumococcal conjugates are as disclosed above for meningococcal conjugates, including choice of carrier protein (e.g. CRM 197 or tetanus toxoid), linkages, ratios, etc. Where a composition includes more than one conjugate, each conjugate may use the same carrier protein or a different carrier protein. Reference 73 describes potential advantages when using different carrier proteins in multi-valent pneumococcal conjugate vaccines.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 74-80, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [81,82] or similar methods), or they can be predicted (e.g. using the Jameson-Wolf antigenic index [83], matrix-based approaches [84], MAP-ITOPE [85], TEPITOPE [86,87], neural networks [88], OptiMer & EpiMer [89, 90], ADEPT [91], Tsites [92], hydrophilicity [93], antigenic index [94] or the methods disclosed in references 95-99. etc.). Epitopes are the parts of an antigen that are recognised by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 100. A preferred alignment is determined by the Smith-Waterman homology search algorithm using an affine gap search with a gap open penalty of 12 and a gap extension penalty of 2. BLOSUM matrix of 62. The Smith-Waterman homology search algorithm is disclosed in ref. 101.

The word "substantially" does not exclude "completely" e.g. a composition which is "substantially free" from Y may be completely free from Y. Where necessary, the word "substantially" may be omitted from the definition of the invention.

BRIEF DESCRIPTION OF DRAWINGS

FIG. 4C-FIG. 4D shows expression of NadA and NadR in 7 strains, in the presence of absence of 4HPA.

MODES FOR CARRYING OUT THE INVENTION

NHBA

The endogenous nhba gene is knocked out in various serogroup B strains to create strains MC58Δnhba, 95N477Δnhba, NGH38Δnhba and UK013Δnhba. These strains are then transformed with pCOMPpind-287 vector containing a gene encoding nhba from strain 394/98, with or without an upstream CREN (contact regulatory element of Neisseria), under the control of an IPTG-inducible promoter. The vectors insert the nhba gene (±CREN) between the endogenous nmb1428 and nmb1429 genes by homologous recombination.

Figure 5A:
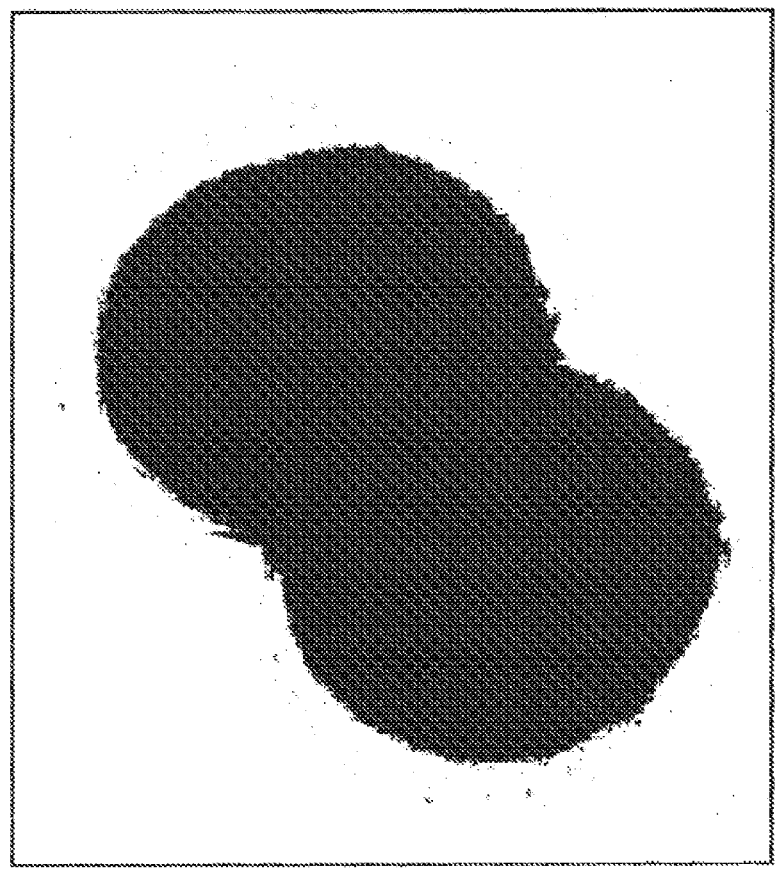
FIG. 5A-FIG. 5C shows (FIG. 5A) starting strain MC58 (FIG. 5B) MC58Δnhba and (FIG. 5C) MC58Δnhba transformed with a complementing nhba gene with an upstream CREN and IPTG-inducible promoter.
Figure 5B:
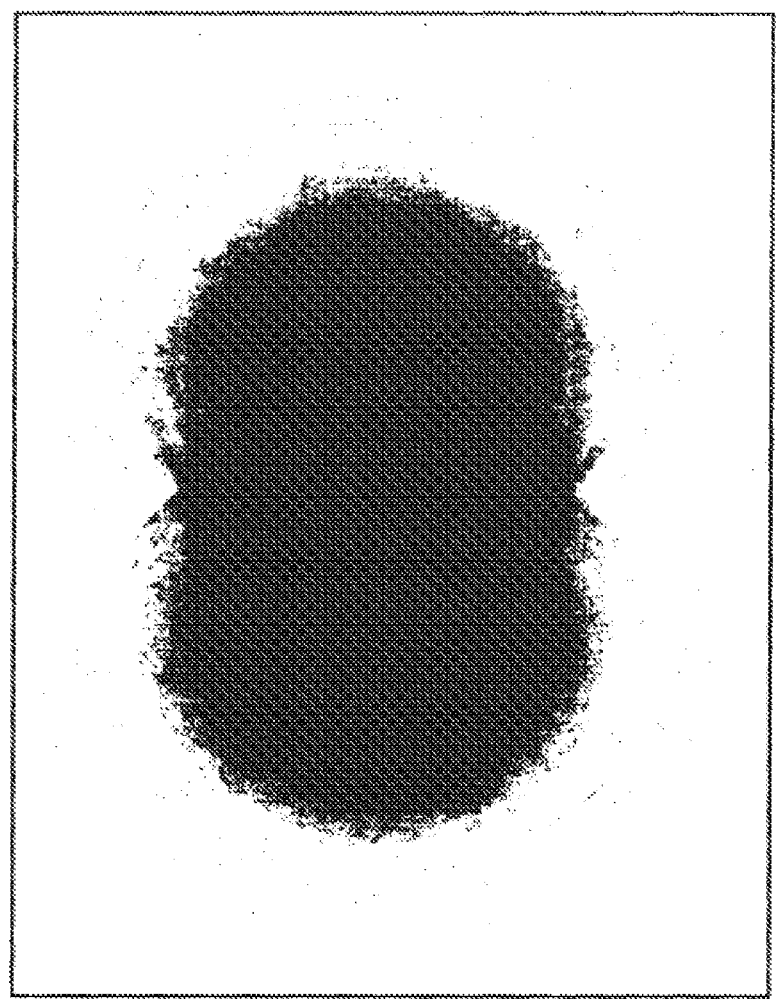
Figure 5C:
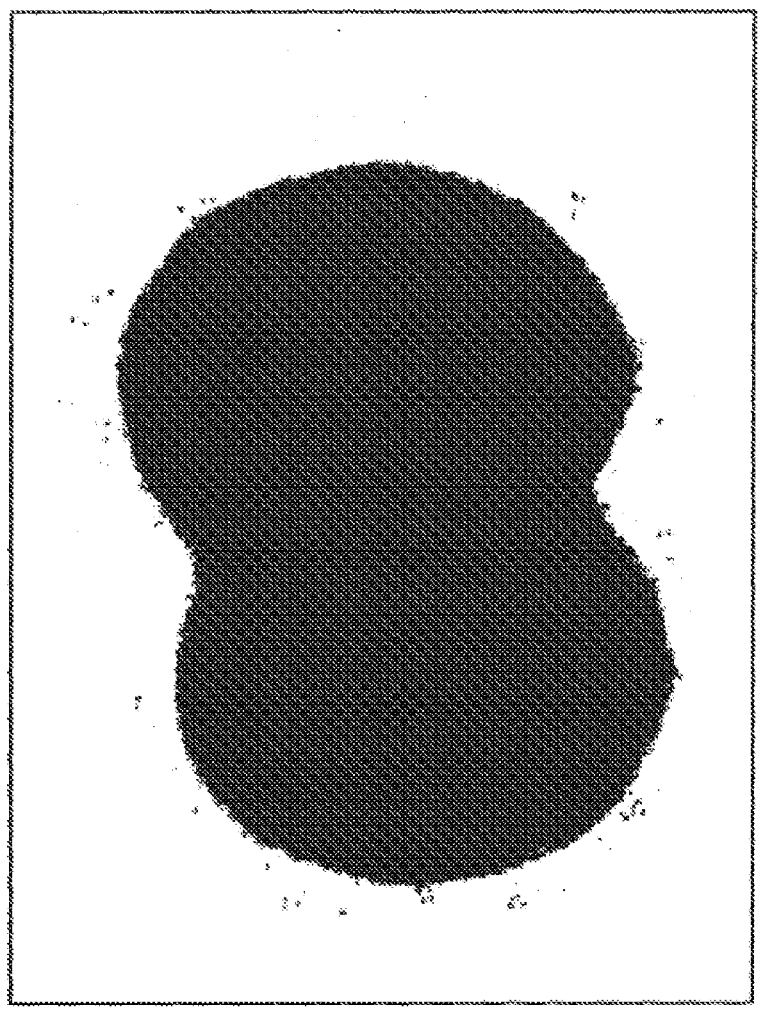
Figure 6:
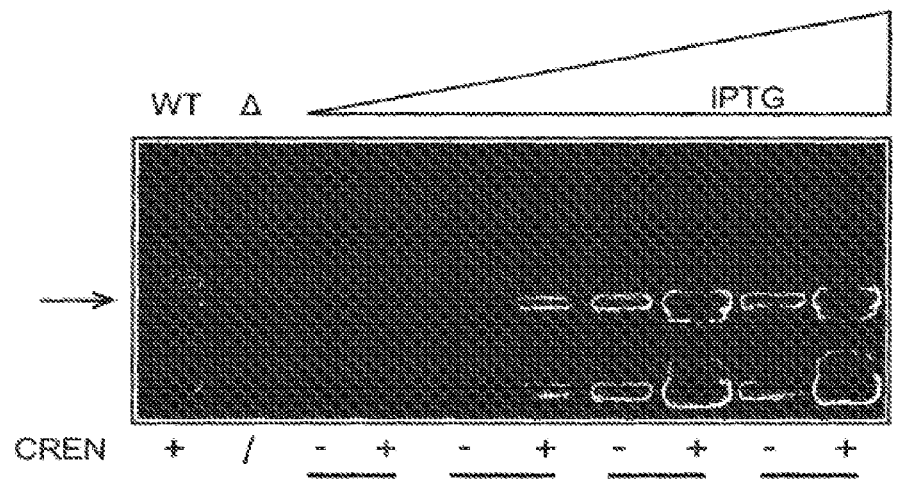
FIG. 6 shows NHBA expression by MC58 and derivative strains. The left two lanes show expression in MC58 and MC58Δnhba. The next 8 lanes show expression in complemented strains at four concentrations of IPTG. The lanes are arranged in pairs, with the right-hand lane being a strain complemented with nhba having an upstream CREN.

FIG. 5 shows the starting MC58 strain, the MC58Δnhba strain, and the complemented MC58 strain (+CREN). FIG. 6 shows expression of NHBA by the various MC58 strains with increasing IPTG concentration. The complemented strains show high levels of inducible NHBA expression, with the highest levels seen with the inserted gene has an upstream CREN.

Figure 7:
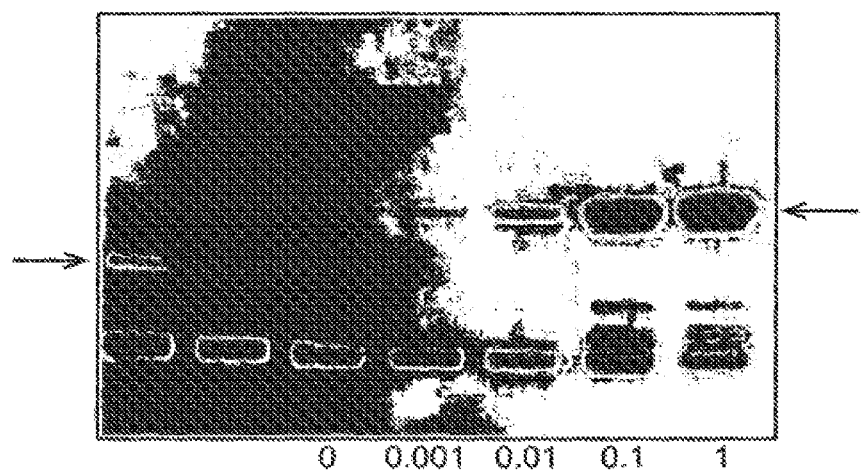
FIG. 7 shows NHBA expression by 95N477 and derivative strains. The left two lanes show expression in 95N477 and 95N477Δnhba. The next 5 lanes show expression in complemented strains at the indicated concentrations of IPTG.

FIG. 7 shows expression in the 95N477 strains. The endogenous nhba gene in this strain encodes a 427aa protein, whereas the inserted complementing gene has 492aa. Increased expression levels of the larger NHBA protein are clearly visible, and this expression increases with IPTG concentration.

Although in some strains (e.g. M4407) it was not possible to obtain a Δnhba knockout using the transformation protocols, for strains which could be transformed these results show that strains which over-express NHBA can readily be obtained.

NadR (NMB 1843)

The nadA gene is present in approximately 50% of meningococcal isolates. NadA exhibits growth-phase dependent expression, with maximal levels in the stationary growth phase of all strains tested. Expression is controlled by a tetranucleotide repeat (TAAA) located upstream of the nadA promoter. The number of repeats can be modified during replication through slipped strand mispairing, and consequently can influence the expression of the nadA gene by creating variants where changes in the repeat number result in promoters with low, medium or high activity.

An area of the nadA promoterm upstream of the TAAA repeat, is responsible for repression of nadA expression during logarithmic phase of growth. This area is called the 'PR region'. DNA-affinity fractionation identified a protein present in meningococcus crude extracts which binds to the GPR region. This protein is NadR (NMB1843) and is a member of the MarR family of repressors. NadR binds to three operators (binding sites) in the nadA promoter and results in repression of NadA expression. Knockout of NadR in strains expressing high, medium or low levels of NadA results in almost comparable high level expression in each strain. Thus NadR is the repressor that contributes to the differential expression levels exhibited by meningococcal strains, or phase variants in the same strain, with different numbers of repeats in their promoter. NadR is expressed to similar levels in different strains but can repress more or less efficiently the nadA promoter depending on the number of repeats present in the variant promoter.

Figure 1:
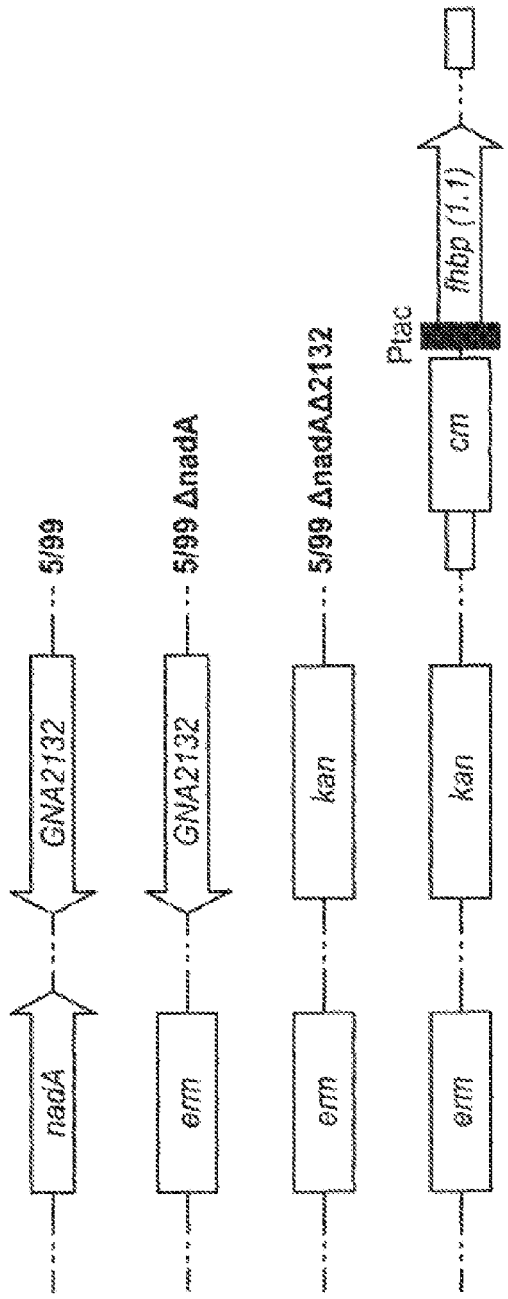
FIG. 1 illustrates the approach for constructing an isogenic panel by knocking out nadA and nhba (GNA2132) to create a background strain.
Figure 2:
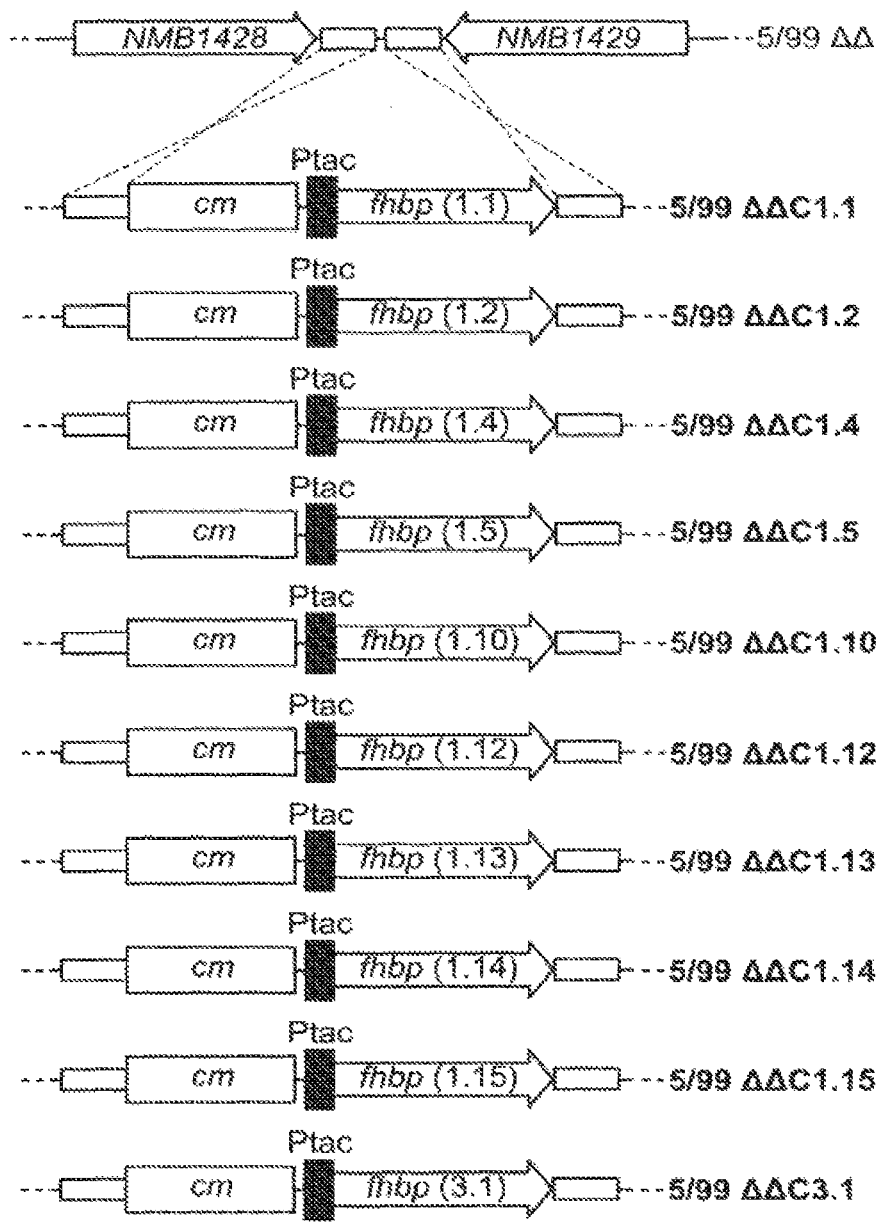
FIG. 2 shows the insertion of fHbp genes into the background strain to make a panel of isogenic strains expressing different fHbp genes under the control of a Ptac promoter.
Figure 3A:
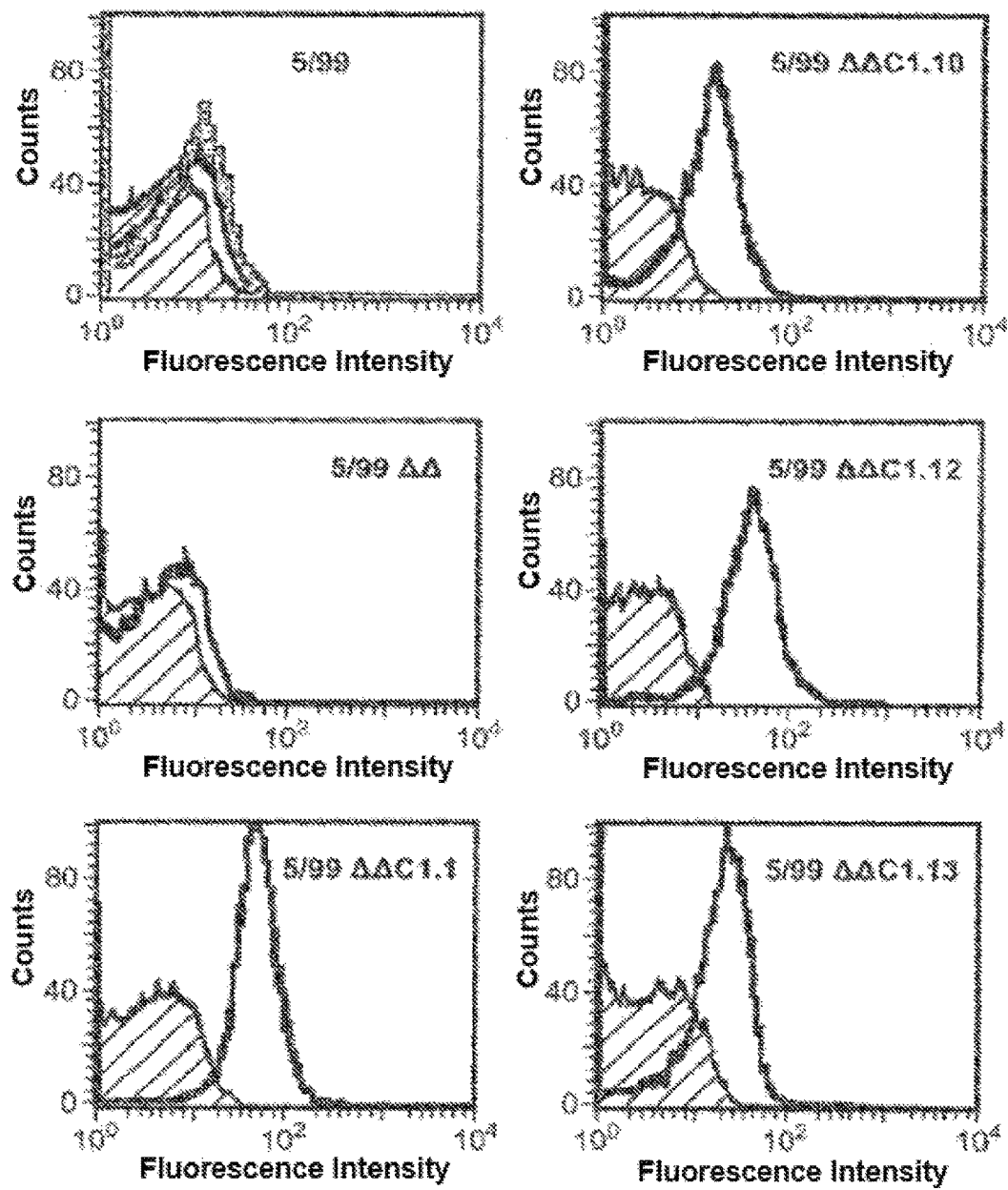
FIG. 3A-FIG. 3B shows expression levels of fHbp in the isogenic panel strains described in FIG. 2.
Figure 3B:
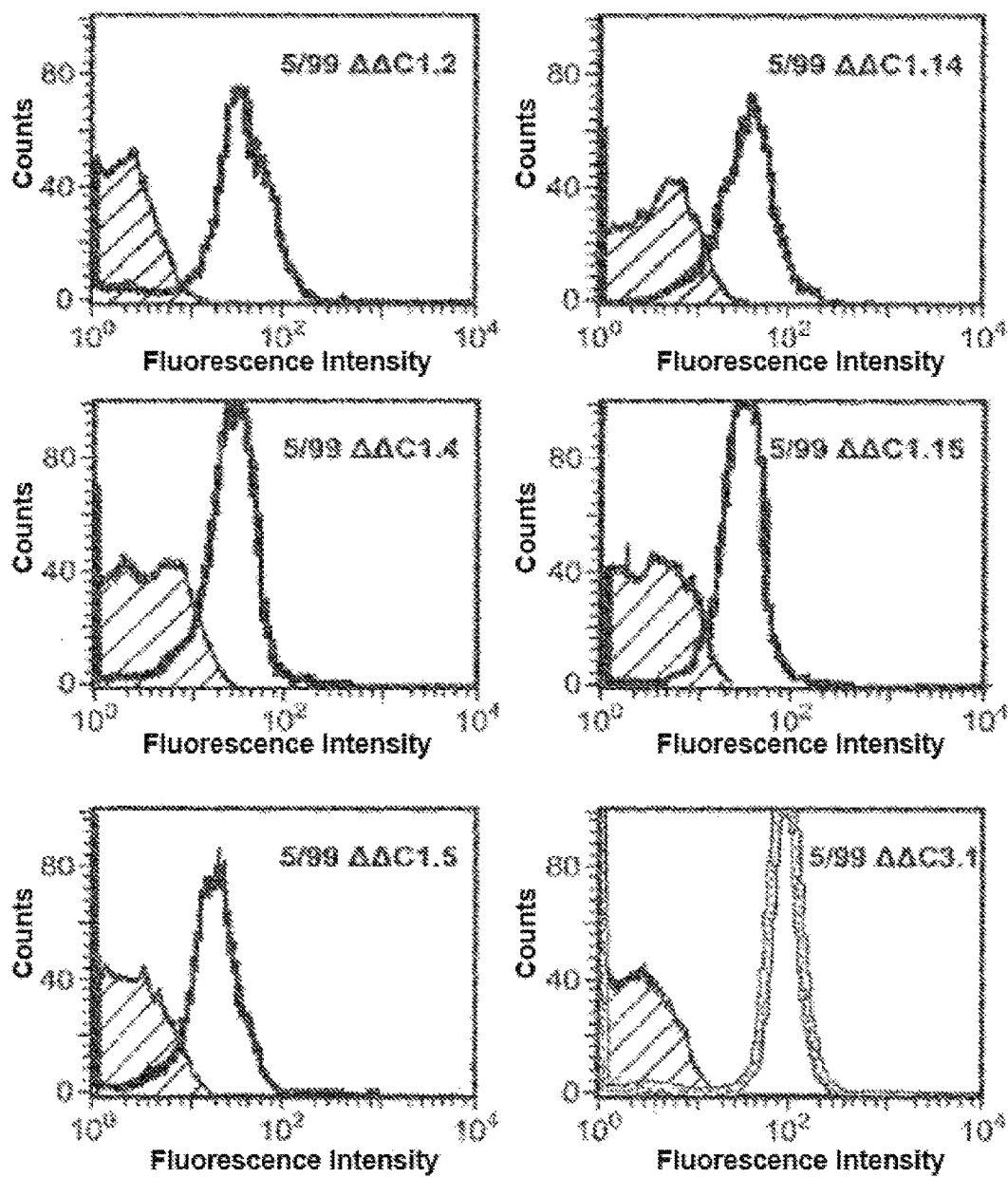
Figure 4A:
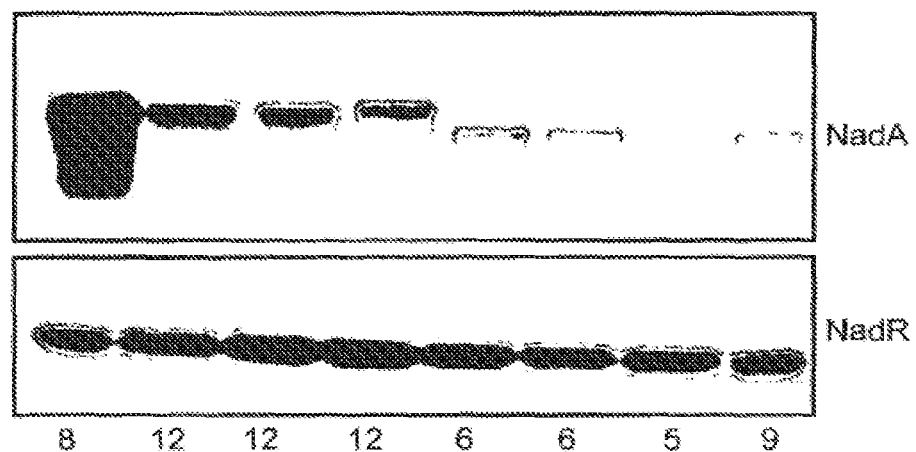
FIG. 4A-FIG. 4B shows expression of NadA (upper panel) and NadR (lower panel) in eight wild-type strains (FIG. 4A) or their NadR knockout forms (FIG. 4B). The numbers in FIG. 4A show the number of TAAA tetranucleotide repeats in the strain.
Figure 4B:
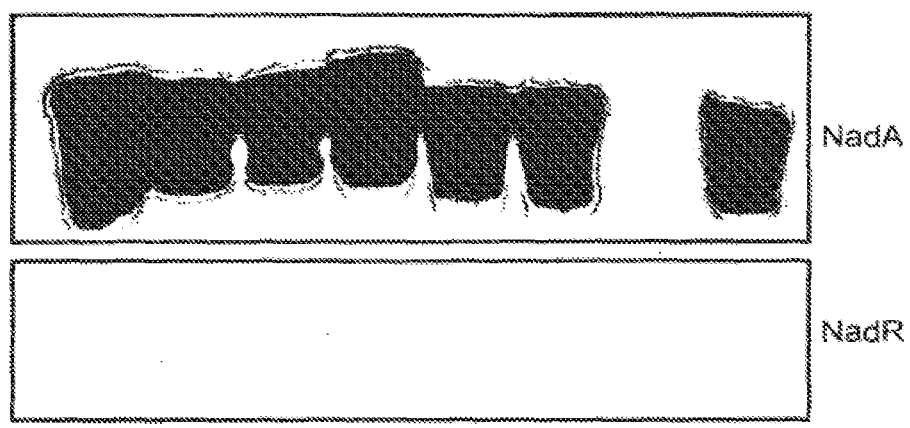

Knockout of NadR in various meningococcus backgrounds results in almost comparable high levels of expression of NadA across the panel. Strains are transformed with the knockout construct for the allelic replacement of nmb1843 with a chloramphenicol cassette. Expression levels in eight different strains are shown in FIG. 4.

Figure 4C:
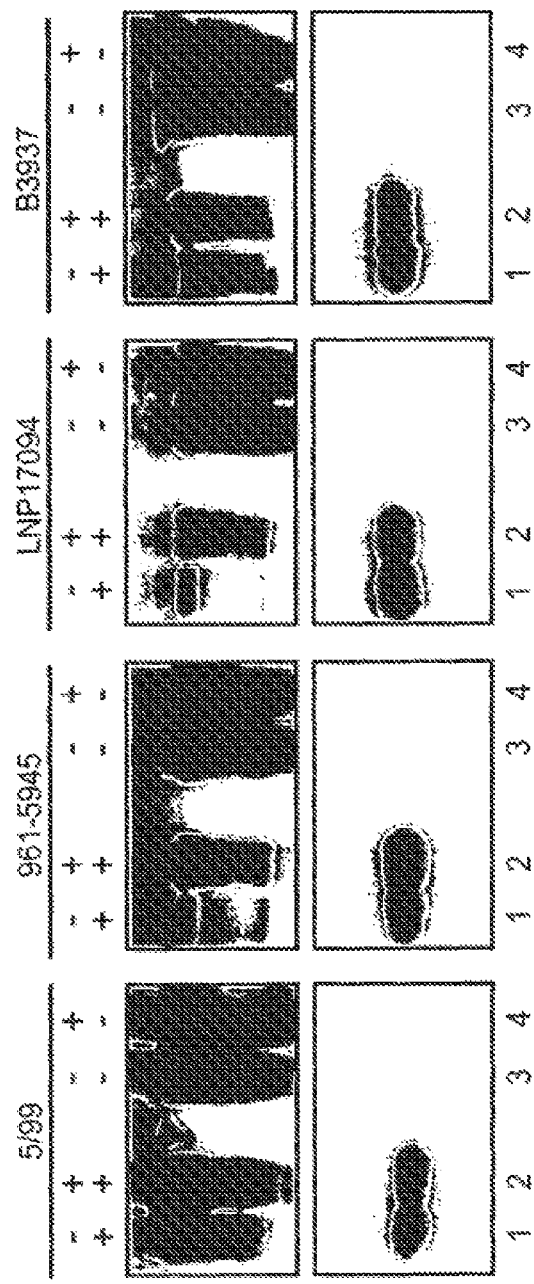
Figure 4D:
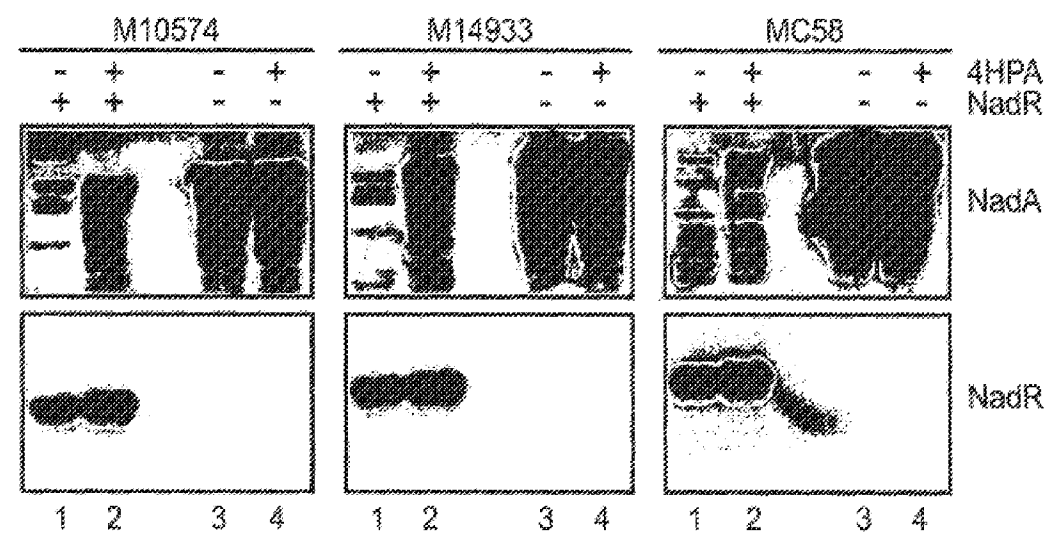

A small molecule ligand 4-hydroxyphenylacetic acid (4HPA) can induce NadA expression in vitro due to derepression of NadR (FIG. 4C). Addition of the molecule to the purified NadR protein in vitro can inhibit the binding activity of the protein for the nadA promoter. 4HPA is a metabolite of the catabolic pathway of the aromatic amino acids and is secreted in human saliva and urine, and so in vivo expression of NadA may be higher than is seen during in vitro growth.

Thus strains which over-express NadA can readily be obtained by inactivation of NadR and/or by addition of a small molecule inducer to the growth medium.

Isogenic Panel—NHBA

NHBA is an antigen in the 4CMenB product. An isogenic panel was used to study the potential cross protection of NHBA-induced bactericidal antibodies.

The nhba genes from six different meningococcal strains were amplified to provide the mature form of the polypeptide with a C-terminis histidine tag. These were cloned into the pET-21b+ plasmid vector and expressed in E.coli. The purified NHBA peptides were then used to immunize mice (20 μg dose) and obtain mouse antisera. ELISA assays were performed in order to confirm the presence of antibodies in all the mouse sera obtained.

To evaluate the immunogenicity and the contribution of amino acid sequence variability to vaccine coverage, a starting strain was engineered to be susceptible to bactericidal killing only by anti-NHBA antibodies (rather than the other antigens in 4CMenB). N.meningitidis strain 5/99 naturally expresses high levels of NadA, but very low levels of NHBA and fHbp. Its nadA and nhba genes were respectively replaced by ery and kan resistance cassettes (5/99ΔΔ). The nhba gene to be complemented was then inserted in the intergenic region between the open reading frames nmb1428 and nmb1429. Thus the final strain panel was isogenic except for the chosen nhba gene, and this gene should be inducable for expression at equal levels in all members of the panel.

Figure 8:
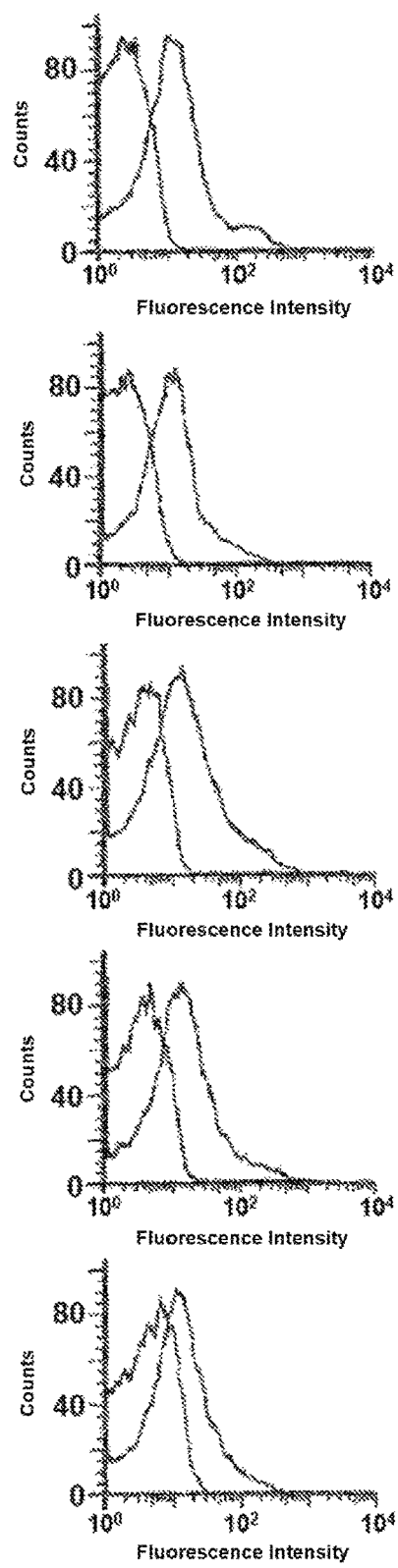
FIG. 8 shows NHBA expression for five strains in an isogenic panel. From top to bottom the expressed NHBA is from strain NZ98/254, UK013, UK355, 2996 and NM117.

FACS showed that the panel members showed a comparable amount of the different NHBA polypeptides in each strain (FIG. 8). Several mouse antisera raised against the different NHBA polypeptides were tested in western blot and the detection appeared to be variant-specific, showing a stronger recognition for the homologous variant.

The panel was also used for testing the bactericidal effect of the mouse antisera. As the strains were isogenic then any difference in bactericidal effect should arise only from the different expressed NHBA polypeptides. In parallel the sera were tested against wild-type strains which express the relevant NHBA polypeptide sequence, to see if the common genetic background of the isogenic panel did enable the detection of differences which would be concealed by natural variation if wild-type strains were used. Results were as follows:

| Antiserum NHBA | 5/99ΔΔ | Wild-type |
|---|---|---|
| NZ98/254 | >8192 | 8192 |
| MC58 | 8192 | 512 |
| UK013 | 256 | 128 |

| Antiserum NHBA | 5/99ΔΔ | Wild-type |
|---|---|---|
| UK355 | 128 | 256 |
| 2996 | 128 | 256 |
| NM117 | 2048 | 4096 |

Thus the panel does seem to compensate for variability which is unrelated to the NHBA antigen itself. For instance, serum raised against the MC58 sequence is much more effective against the MC58 polypeptide in the isogenic panel than against the wild-type MC5B strain.

Isogenic Panel—fHbp

Sequencing of the fHbp gene in a large collection of meningococcal isolates revealed three variants with low levels of cross-protective bactericidal response. A serum bactericidal assay was used to evaluate the cross-protective capabilities of human antibodies raised against different fHbp variants, but the killing mediated by bactericidal antibodies in this assay is dependent by several factors. Thus the potential coverage of a single antigen may be difficult to estimate.

A genetic approach was used to overcome variability due to strain-specific serum susceptibility, limitations of compatible complement sources, and variable expression of fHbp and other surface-exposed factors affecting resistance to serum (e.g. the capsule). A well-characterized meningococcal isolate (5/99) was engineered to generate isogenic strains expressing ten different fHbp sub-variants from a constitutive heterologous promoter. The fHbp genes were inserted between endogenous nmb1428 and nmb1429 genes. This panel was then used as the test strain in a serum bactericidal antibody (SBA) assay to assess the ability of a single fHbp variant to elicit a broadly-protective immune response.

In order to have a genetic background to express different fHbp sub-variants without the interfering action of the other antigens, the nadA and nhba genes in the starting 5/99 strain were inactivated by insertion of erm and kan resistance cassettes, respectively (FIG. 1). The resulting double mutant strain (named 5/99ΔΔ) was manipulated to express different fHbp subvariants under the control of a Ptac promoter to standardize the amount of fHbp expressed (FIG. 1 and FIG. 2). In total, ten different fHbp coding sequences were cloned in the pComp-RBS vector and transferred to the 5/99ΔΔ genetic background.

To evaluate the expression of fHbp in the recombinant strains, we performed FACS analysis using a mouse polyclonal scrum against a single fHbp variant. The analysis showed a comparable amount of the different fHbp subvariants on the surface of the recombinant strains generated (FIG. 3).

The recombinant strains were analyzed for their susceptibility to killing by bactericidal antibodies from mice in a SBA using rabbit complement. Pooled sera from mice immunized with the "universal vaccine" of reference 19 or with its GNA2091-fHbp component were tested for their ability to kill the 5/99 wild-type, the intermediate 5/99ΔΔ strain expressing neither NHBA nor NadA antigens, and the ten recombinant strains. The 5/99 strain was killed by sera raised against the universal vaccine, but not by sera raised against the single antigen GNA2091-fHbp. The 5/99ΔΔ strain was resistant to killing by all sera. All of the complemented strains except one showed significant susceptibility to sera derived from mice immunized with the universal vaccine or with GNA2091-fHbp antigen. The single surviving strain expressed a fHbp in family III, confirming the absence of cross-reactivity between the fHbp families. The nine susceptible strains confirm that the specific fHbp sequence in the universal vaccine can raise antibodies which are broadly protective across the whole of fHbp family I.

The panel was also tested using sera obtained from human adults who were immunised with 4CMenB. The results were comparable to those seen using mice.

It will be understood that the invention is described above by way of example only and modifications may be made whilst remaining within the scope and spirit of the invention.

REFERENCES

[1] Claassen et al. (1996) *Vaccine* 14:1001-8.
[2] Koeberling et al. (2007) *Vaccine* 25:1912-20.
[3] Koeberling et al. (2008) *J Infect Dis* 198:262-70.
[4] Hou et al. (2005) *J Infect Dis* 192:580-90.
[5] WO2009/038889.
[6] Bonvehi et al. (2010) *Clin Vacc Immunol* 17:1460-6.
[7] Zollinger et al. (2010) *Vaccine* 28:5057-67.
[8] WO2004/015099.
[9] WO2006/081259.
[10] Deghmane et al. (2003) *Infect Immun* 71:2897-901.
[11] Serruto et al. (2010) *PNAS USA* 107:3770-5.
[12] Schielke et al. (2009) *Mol Microbiol* 72:1054-67.
[13] WO2004/014418.
[14] WO00/25811.
[15] WO2010/070453.
[16] WO02/09746.
[17] Oriente et al. (2010) *J Bacterial* 192:691 -701.
[18] U.S. provisional patent application 61/247,428.
[19] Giuliani et al. (2006) *Proc Natl Acad Set USA* 103(29): 10834-9.
[20] Donnelly et al. (2010) *PNAS USA* 107:19490-5.
[21] Kimura et al. (2010) *Clin Vaccine Immunol* 2010 PMID: 21177912.
[22] WO02/09643.
[23] Katial et al. (2002) *Infect. Immun.* 70:702-707.
[24] U.S. Pat. No. 6,180,111.
[25] WO01/34642.
[26] WO2004/019977.
[27] European patent 0011243.
[28] Fredriksen et al. (1991) *NIPH Ann.* 14(2):67-80.
[29] WO01/91788.
[30] WO2005/004908.
[31] WO2006/046143.
[32] WO00/26384.
[33] U.S. Pat. No. 6,531,131
[34] U.S. Pat. No. 6,645,503
[35] de Kleijn et al. (2000) *Vaccine* 18:1456-66.
[36] WO03/105890.
[37] WO2006/024946
[38] WO99/10497.
[39] Steeghs et al. (2001) *The EMBO Journal* 20:6937-6945.
[40] Maiden et al. (1998) *PNAS USA* 95:3140-3145.
[41] WO01/09350.
[42] WO02/062378.
[43] WO2004/014417.
[44] WO00/66741.
[45] WO99/57280
[46] U.S. Pat. No. 5,698,438.
[47] Perkins-Balding et al. (2003) *Microbiology* 149:3423-35.
[48] Masignani et al. (2003) *J Exp Med* 197:789-799.
[49] Welsch et al (2004) *J Immunol* 172:5605-15.
[50] Hou et al. (2005) *J Infect Dis* 192(4): 580-90.

[51] WO03/063766.
[52] Fletcher et al (2004) *Infect Immun* 72:2088-2100.
[53] Zhu et al. (2005) *Infect Immun* 73(10):6838-45.
[54] Cantini et al. (2006) *J. Biol. Chem.* 281:7220-7227
[55] WO2004/048404
[56] WO2009/104097.
[57] Martin et al. (1997) *J Exp Med* 185(7):1173-83.
[58] WO96/29412.
[59] WO01/55182.
[60] WO01/38350.
[61] WO00/23595.
[62] Gennaro (2000) *Remington: The Science and Practice of Pharmacy.* 20th edition. ISBN: 0683306472.
[63] RIVM report 124001 004.
[64] RIVM report 000012 003.
[65] *Vaccine Design . . .* (1995) eds. Powell & Newman. ISBN: 030644867X. Plenum.
[66] WO01/30390.
[67] neisseria.org/nm/typing/mist/
[68] Tettelin et al. (2000) *Science* 287:1809-1815.
[69] Pettersson el al. (1994) *Microb Pathog* 17(6):395-408.
[70] Welsch et al. (2002) Thirteenth International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria, meningitidis strains.*
[71] Santos et al. (2002) Thirteenth International Pathogenic Neisseria Conference. Norwegian Institute of Public Health. Oslo, Norway; Sep. 1-6, 2002. *Serum bactericidal responses in rhesus macaques immunized with novel vaccines containing recombinant proteins derived from the genome of N. meningitidis.*
[72] WO2007/000327.
[73] WO2007/071707
[74] *Methods In Enzymology* (S. Colowick and N. Kaplan, eds., Academic Press, Inc.)
[75] *Handbook of Experimental Immunology*, Vols. I-IV (D. M, Weir and C. C. Black well, eds, 1986, Blackwell Scientific Publications)
[76] Sambrook et al (2001) *Molecular Cloning: A Laboratory Manual* 3rd edition (Cold Spring Harbor Laboratory Press).
[77] *Handbook of Surface and Colloidal Chemistry* (Birds, K. S. ed., CRC Press, 1997)
[78] Ausubel et al. (eds) (2002) *Short protocols in molecular biology*, 5th edition (Current Protocols).
[79] *Molecular Biology Techniques: An Intensive Laboratory Course*, (Ream et al. eds., 1998, Academic Press)
[80] *PCR (Introduction to Biotechniques Series)*, 2nd ed. (Newton & Graham eds., 1997, Springer Verlag)
[81] Geysen et al. (1984) *PNAS USA* 81:3998-4002.
[82] Carter (1994) *Methods Mol Biol* 36:207-23.
[83] Jameson, B A et al. 1988. CABIOS 4(1):181-186.
[84] Raddrizzani & Hammer (2000) *Brief Bioinform* 1(2): 179-89.
[85] Bublil et al. (2007) *Proteins* 68(1):294-304.
[86] De Lalla et al. (1999) *J. Immunol* 163:1725-29.
[87] Kwok et al. (2001) *Trends Immunol* 22:583-88.
[88] Brusic et al. (1998) *Bioinformatics* 14(2):121-30
[89] Meister et al. (1995) *Vaccine* 13(6):581-91.
[90] Roberts et al. (1996) *AIDS Res Hum Retroviruses* 12(7): 593-610.
[91] Maksyutov & Zagrebelnaya (1993) *Comput Appl Biosci* 9(3):291-7.
[92] Feller & de la Cruz (1991) *Nature* 349(6311):720-1.
[93] Hopp (1993) *Peptide Research* 6:183-190.
[94] Welling et al. (1985) FEBS Lett. 188:215-218.
[95] Davenport et al. (1995) *Immunogenics* 42:392-297.
[96] Tsurui & Takahashi (2007) *J Pharmacol Sci.* 105(4): 299-316.
[97] Tong et al. (2007) *Brief Bioinform.* 8(2):96-108.
[98] Schirle et al. (2001) *J Immunol Methods.* 257(1-2):1-16.
[99] Chen et al. (2007) *Amino Acids* 33(3):423-8.
[100] *Current Protocols in Molecular Biology* (F. M. Ausubel et al, eds., 1987) Supplement 30
[101] Smith & Waterman (1981) *Adv. Appl. Math.* 2: 482-489.

We claim:

1. A modified meningococcus bacterium which expresses
   (i) Neisserial Heparin Binding Antigen (NHBA), wherein expression of NHBA is controlled by an inducible or constitutive promoter and wherein the promoter optionally includes a Contact Regulatory Element of Neisseria (CREN), or
   (ii) NHBA and Neisserial adhesion A (NadA), wherein expression of NHBA is controlled by an inducible or constitutive promoter and wherein the promoter optionally includes a CREN, and wherein the bacterium does not express Neisserial adhesion A regulator (NadR).

2. The modified meningococcus bacterium of claim 1, which also over-expresses factor H binding protein (fHbp).

3. The modified meningococcus bacterium of claim 1, wherein the modified meningococcus bacterium is isogenic with an unmodified meningococcus bacterium, except for a genetic modification which causes the modified meningococcus bacterium to express more NHBA, or more of both NHBA and NadA than the unmodified meningococcus bacterium.

4. The modified meningococcus bacterium of claim 3, which includes (i) a gene under the control of a promoter which does not control that gene in the unmodified meningococcus bacterium, (ii) a knockout of a gene which is found in the unmodified meningococcus bacterium, or (iii) both (i) and (ii).

5. The modified meningococcus bacterium of claim 3, wherein the modified meningococcus bacterium also expresses more fHbp than the unmodified meningococcus bacterium.

6. The modified meningococcus bacterium of claim 1, wherein expression of NHBA is controlled by a strong promoter, NadR is knocked out, and the modified meningococcus bacterium expresses a constitutively active mutant Fumarate and Nitrate reductase Regulator protein (FNR).

7. The modified meningococcus bacterium of claim 1, wherein expression of NHBA is controlled by a strong promoter, expression of fHbp is controlled by a strong promoter, and NadR is knocked out.

8. The modified meningococcus bacterium of claim 1, wherein the modified meningococcus bacterium has a knockout of Lipid A biosynthesis lauroyl acyltransferase (LpxL1).

9. The modified meningococcus bacterium of claim 1, wherein the modified meningococcus bacterium does not express an active Membrane-bound lytic transglycosylase A (MltA).

10. The modified meningococcus bacterium of claim 1, wherein the modified meningococcus bacterium does not express Porin A (PorA).

11. The modified meningococcus bacterium of claim 1, wherein the modified meningococcus bacterium does not express Iron-repressed protein B (FrpB).

12. The modified meningococcus bacterium of claim 1, wherein the modified meningococcus bacterium is serogroup B.

13. The modified meningococcus bacterium of claim 1, where the modified meningococcus bacterium is immunotype L3.

14. A process for preparing the modified meningococcus bacterium of claim 1, comprising steps of (i) choosing a starting meningococcus bacterium which expresses NHBA, or both NadA and NHBA; and (ii) modifying the starting meningococcus bacterium (a) so that expression of NHBA is controlled by an inducible or constitutive promoter, wherein the promoter optionally includes a CREN, and thereby increase the amount of NHBA which it expresses, or (b) to not express NadR, thereby increase the amount of NadA which it expresses, and modifying the starting meningococcus bacterium so that expression of NHBA is controlled by an inducible or constitutive promoter, wherein the promoter optionally includes a CREN, and thereby increase the amount of NHBA which it expresses.

15. A process for preparing a modified meningococcus bacterium, comprising steps of (i) choosing a starting meningococcus bacterium which expresses a first amount of NHBA, or a first amount of both NHBA and NadA when grown in specific culture conditions, then (ii) modifying the starting meningococcus bacterium to provide the modified meningococcus bacterium of claim 1, wherein the modified meningococcus bacterium expresses a second amount of NHBA, or a second amount of both NHBA and NadA when grown in the same specific culture conditions, wherein the second amount is higher than the first amount.

16. The process of claim 15, including a step (iii) culturing the modified meningococcus bacterium obtained in step (ii) to provide a bacterial culture.

17. A process for growing a modified meningococcus bacteria which over-expresses NadA, comprising a step of (i) growing a starting meningococcus bacterium in the presence of 4-hydroxyphenylacetic acid or an analogue thereof which induces NadA expression and optionally (ii) culturing the modified meningococcus bacteria to provide a bacterial culture.

18. A process for preparing a meningococcal outer membrane vesicle (OMV), comprising a step of treating a meningococcal bacterial culture comprising the modified meningococcus bacterium of claim 1 such that its outer membrane forms vesicles.

19. The process of claim 17, further comprising a step of (iii) treating the bacterial culture comprising the modified meningococcus bacteria such that its outer membrane forms vesicles.

20. A method of raising an immune response in a mammal, comprising a step of administering an immunogenic pharmaceutical composition to the mammal wherein the immunogenic composition comprises the OMV prepared by the process of claim 18 and that is from the modified meningococcus bacterium which over-expresses NHBA or both NadA and NHBA.

21. A method of raising an immune response in a mammal, comprising a step of administering an immunogenic composition to the mammal wherein the immunogenic composition comprises the outer membrane vesicles prepared by the process of claim 19.

* * * * *

SEQUENCE LISTING

```
<160> NUMBER OF SEQ ID NOS: 25

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95
```

```
Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Asp Ile Lys
            180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
210                 215                 220
```

```
Glu Ile Ala Gly Ser Ala Thr Val Lys Ile Gly Glu Lys Val His Glu
225                 230                 235                 240

Ile Gly Ile Ala Gly Lys Gln
            245
```

<210> SEQ ID NO 3
<211> LENGTH: 250
<212> TYPE: PRT
<213> ORGANISM: Neisseria meningitidis

<400> SEQUENCE: 3

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
                180                 185                 190

Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250
```

<210> SEQ ID NO 4
<211> LENGTH: 644
<212> TYPE: PRT
<213> ORGANISM: Artificial Sequence
<220> FEATURE:
<223> OTHER INFORMATION: Hybrid meningococcal antigen

<400> SEQUENCE: 4

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30
```

```
Gln Ala Gly Ser Gln Gly Gln Gly Ala Pro Ser Ala Gln Gly Gly Gln
             35                  40                  45

Asp Met Ala Ala Val Ser Glu Glu Asn Thr Gly Asn Gly Gly Ala Ala
     50                  55                  60

Ala Thr Asp Lys Pro Lys Asn Glu Asp Glu Gly Ala Gln Asn Asp Met
 65                  70                  75                  80

Pro Gln Asn Ala Ala Asp Thr Asp Ser Leu Thr Pro Asn His Thr Pro
                 85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
            115                 120                 125

Asp Gly Met Gln Gly Asp Pro Ser Ala Gly Glu Asn Ala Gly
        130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
```

```
        450                 455                 460
Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
                    500                 505                 510

Phe Asp Gln Ala Lys Arg Asp Gly Lys Ile Asp Ile Thr Ile Pro Val
                515                 520                 525

Ala Asn Leu Gln Ser Gly Ser Gln His Phe Thr Asp His Leu Lys Ser
            530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
        610                 615                 620

Val Asn Val Gly Met Thr Lys Ser Val Arg Ile Asp Ile Gln Ile Glu
625                 630                 635                 640

Ala Ala Lys Gln
```

<210> SEQ ID NO 5
<211> LENGTH: 434
<212> TYPE: PRT
<213> ORGANISM: Artificial Sequence
<220> FEATURE:
<223> OTHER INFORMATION: Hybrid meningococcal antigen

<400> SEQUENCE: 5

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Arg Ala Arg Val Lys Ile Val Thr Tyr Gly Asn Val Thr Tyr
        130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175
```

Tyr Val Gln Arg Gly Ser Gly Gly Gly Val Ala Ala Asp Ile Gly
            180             185             190

Ala Gly Leu Ala Asp Ala Leu Thr Ala Pro Leu Asp His Lys Asp Lys
        195                 200             205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Leu Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
            115                 120                 125

Thr Phe Ala Glu Glu Thr Lys Thr Asn Ile Val Lys Ile Asp Glu Lys
        130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 7
<211> LENGTH: 792
<212> TYPE: PRT
<213> ORGANISM: Neisseria meningitidis

<400> SEQUENCE: 7

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val

-continued

```
            145                 150                 155                 160
Asn Tyr Gln Thr Leu Gln Gly Arg Asp Leu Leu Asp Asp Arg Gln
                    165                 170                 175
Phe Gly Val Met Met Lys Asn Gly Tyr Ser Thr Arg Asn Arg Glu Trp
                    180                 185                 190
Thr Asn Thr Leu Gly Phe Gly Val Ser Asn Asp Arg Val Asp Ala Ala
                    195                 200                 205
Leu Leu Tyr Ser Gln Arg Arg Gly His Glu Thr Glu Ser Ala Gly Asn
210                 215                 220
Arg Gly Tyr Ala Val Glu Gly Glu Gly Ser Gly Ala Asn Ile Arg Gly
225                 230                 235                 240
Ser Ala Arg Gly Ile Pro Asp Ser Ser Lys His Lys Tyr Asn His His
                    245                 250                 255
Ala Leu Gly Lys Ile Ala Tyr Gln Ile Asn Asp Asn His Arg Ile Gly
                    260                 265                 270
Ala Ser Leu Asn Gly Gln Gln Gly His Asn Tyr Thr Val Glu Glu Ser
                    275                 280                 285
Tyr Asn Leu Thr Ala Ser Ser Trp Arg Glu Ala Asp Asp Val Asn Arg
290                 295                 300
Arg Arg Asn Ala Asn Leu Phe Tyr Glu Trp Met Pro Asp Ser Asn Trp
305                 310                 315                 320
Leu Ser Ser Leu Lys Ala Asp Phe Asp Tyr Gln Lys Thr Lys Val Ala
                    325                 330                 335
Ala Val Asn Asn Lys Gly Ser Phe Pro Met Asp Tyr Ser Thr Trp Thr
                    340                 345                 350
Arg Asn Tyr Asn Gln Lys Asp Leu Asp Glu Ile Tyr Asn Arg Ser Met
                    355                 360                 365
Asp Thr Arg Phe Lys Arg Phe Thr Leu Arg Leu Asp Ser His Pro Leu
                    370                 375                 380
Gln Leu Gly Gly Gly Arg His Arg Leu Ser Phe Lys Thr Phe Val Ser
385                 390                 395                 400
Arg Arg Asp Phe Glu Asn Leu Asn Arg Asp Asp Tyr Tyr Phe Ser Gly
                    405                 410                 415
Arg Val Val Arg Thr Thr Ser Ser Ile Gln His Pro Val Lys Thr Thr
                    420                 425                 430
Asn Tyr Gly Phe Ser Leu Ser Asp Gln Ile Gln Trp Asn Asp Val Phe
                    435                 440                 445
Ser Ser Arg Ala Gly Ile Arg Tyr Asp His Thr Lys Met Thr Pro Gln
450                 455                 460
Glu Leu Asn Ala Glu Cys His Ala Cys Asp Lys Thr Pro Pro Ala Ala
465                 470                 475                 480
Asn Thr Tyr Lys Gly Trp Ser Gly Phe Val Gly Leu Ala Ala Gln Leu
                    485                 490                 495
Asn Gln Ala Trp Arg Val Gly Tyr Asp Ile Thr Ser Gly Tyr Arg Val
                    500                 505                 510
Pro Asn Ala Ser Glu Val Tyr Phe Thr Tyr Asn His Gly Ser Gly Asn
                    515                 520                 525
Trp Leu Pro Asn Pro Asn Leu Lys Ala Glu Arg Ser Thr Thr His Thr
                    530                 535                 540
Leu Ser Leu Gln Gly Arg Ser Glu Lys Gly Met Leu Asp Ala Asn Leu
545                 550                 555                 560
Tyr Gln Ser Asn Tyr Arg Asn Phe Leu Ser Glu Glu Gln Lys Leu Thr
                    565                 570                 575
```

```
Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
        595                 600                 605

Asp Lys Ala Arg Ile Arg Gly Ile Glu Leu Thr Gly Arg Leu Asn Val
610                 615                 620

Asp Lys Val Ala Ser Phe Val Pro Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
        755                 760                 765

Arg Asp Gly Lys Gly Leu Asp Arg Tyr Arg Ala Pro Gly Arg Asn Tyr
770                 775                 780

Ala Val Ser Leu Glu Trp Lys Phe
785                 790

<210> SEQ ID NO 8
<211> LENGTH: 793
<212> TYPE: PRT
<213> ORGANISM: Neisseria meningitidis

<400> SEQUENCE: 8

Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
            20                  25                  30

Pro Val Lys Ala Glu Val Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65              70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
```

```
                145                 150                 155                 160
Asn Tyr Gln Thr Leu Gln Gly Arg Asp Leu Leu Pro Glu Arg Gln
                    165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
                195                 200                 205

Leu Leu Tyr Ser Gln Arg Arg Gly His Glu Thr Glu Ser Ala Gly Lys
210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr Asn His His
                245                 250                 255

Ala Leu Gly Lys Ile Ala Tyr Gln Ile Asn Asp Asn His Arg Ile Gly
                260                 265                 270

Ala Ser Leu Asn Gly Gln Gln Gly His Asn Tyr Thr Val Glu Glu Ser
                275                 280                 285

Tyr Asn Leu Leu Ala Ser Tyr Trp Arg Glu Ala Asp Asp Val Asn Arg
                290                 295                 300

Arg Arg Asn Thr Asn Leu Phe Tyr Glu Trp Thr Pro Glu Ser Asp Arg
305                 310                 315                 320

Leu Ser Met Val Lys Ala Asp Val Asp Tyr Gln Lys Thr Lys Val Ser
                325                 330                 335

Ala Val Asn Tyr Lys Gly Ser Phe Pro Ile Glu Asp Ser Ser Thr Leu
                340                 345                 350

Thr Arg Asn Tyr Asn Gln Lys Asp Leu Asp Glu Ile Tyr Asn Arg Ser
                355                 360                 365

Met Asp Thr Arg Phe Lys Arg Ile Thr Leu Arg Leu Asp Ser His Pro
                370                 375                 380

Leu Gln Leu Gly Gly Gly Arg His Arg Leu Ser Phe Lys Thr Phe Ala
385                 390                 395                 400

Ser Arg Arg Asp Phe Glu Asn Leu Asn Arg Asp Asp Tyr Tyr Phe Ser
                405                 410                 415

Gly Arg Val Val Arg Thr Thr Ser Ser Ile Gln His Pro Val Lys Thr
                420                 425                 430

Thr Asn Tyr Gly Phe Ser Leu Ser Asp Gln Ile Gln Trp Asn Asp Val
                435                 440                 445

Phe Ser Ser Arg Ala Gly Ile Arg Tyr Asp His Thr Lys Met Thr Pro
450                 455                 460

Gln Glu Leu Asn Ala Glu Cys His Ala Cys Asp Lys Thr Pro Pro Ala
465                 470                 475                 480

Ala Asn Thr Tyr Lys Gly Trp Ser Gly Phe Val Gly Leu Ala Ala Gln
                485                 490                 495

Leu Asn Gln Ala Trp Arg Val Gly Tyr Asp Ile Thr Ser Gly Tyr Arg
                500                 505                 510

Val Pro Asn Ala Ser Glu Val Tyr Phe Thr Tyr Asn His Gly Ser Gly
                515                 520                 525

Asn Trp Leu Pro Asn Pro Asn Leu Lys Ala Glu Arg Thr Thr Thr His
                530                 535                 540

Thr Leu Ser Leu Gln Gly Arg Ser Glu Lys Gly Thr Leu Asp Ala Asn
545                 550                 555                 560

Leu Tyr Gln Ser Asn Tyr Arg Asn Phe Leu Ser Glu Glu Gln Lys Leu
                565                 570                 575
```

```
Thr Thr Ser Gly Asp Val Ser Cys Thr Gln Met Asn Tyr Tyr Tyr Gly
            580                 585                 590

Met Cys Ser Asn Pro Tyr Ser Glu Lys Leu Glu Trp Gln Met Gln Asn
        595                 600                 605

Ile Asp Lys Ala Arg Ile Arg Gly Ile Glu Leu Thr Gly Arg Leu Asn
610                 615                 620

Val Asp Lys Val Ala Ser Phe Val Pro Glu Gly Trp Lys Leu Phe Gly
625                 630                 635                 640

Ser Leu Gly Tyr Ala Lys Ser Lys Leu Ser Gly Asp Asn Ser Leu Leu
                645                 650                 655

Ser Thr Gln Pro Leu Lys Val Ile Ala Gly Ile Asp Tyr Glu Ser Pro
            660                 665                 670

Ser Glu Lys Trp Gly Val Phe Ser Arg Leu Thr Tyr Leu Gly Ala Lys
        675                 680                 685

Lys Val Lys Asp Ala Gln Tyr Thr Val Tyr Glu Asn Lys Gly Trp Gly
690                 695                 700

Thr Pro Leu Gln Lys Lys Val Lys Asp Tyr Pro Trp Leu Asn Lys Ser
705                 710                 715                 720

Ala Tyr Val Phe Asp Met Tyr Gly Phe Tyr Lys Pro Val Lys Asn Leu
                725                 730                 735

Thr Leu Arg Ala Gly Val Tyr Asn Val Phe Asn Arg Lys Tyr Thr Thr
            740                 745                 750

Trp Asp Ser Leu Arg Gly Leu Tyr Ser Tyr Ser Thr Thr Asn Ser Val
        755                 760                 765

Asp Arg Asp Gly Lys Gly Leu Asp Arg Tyr Arg Ala Pro Ser Arg Asn
770                 775                 780

Tyr Ala Val Ser Leu Glu Trp Lys Phe
785                 790

<210> SEQ ID NO 9
<211> LENGTH: 488
<212> TYPE: PRT
<213> ORGANISM: Neisseria meningitidis

<400> SEQUENCE: 9

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
        50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
130                 135                 140

Asp Met Ala Asn Ala Ala Asp Gly Met Gln Gly Asp Asp Pro Ser Ala
```

```
                145                 150                 155                 160
Gly Gly Gln Asn Ala Gly Asn Thr Ala Ala Gln Gly Ala Asn Gln Ala
                165                 170                 175
Gly Asn Asn Gln Ala Ala Gly Ser Ser Asp Pro Ile Pro Ala Ser Asn
                180                 185                 190
Pro Ala Pro Ala Asn Gly Gly Ser Asn Phe Gly Arg Val Asp Leu Ala
                195                 200                 205
Asn Gly Val Leu Ile Asp Gly Pro Ser Gln Asn Ile Thr Leu Thr His
    210                 215                 220
Cys Lys Gly Asp Ser Cys Ser Gly Asn Asn Phe Leu Asp Glu Glu Val
225                 230                 235                 240
Gln Leu Lys Ser Glu Phe Glu Lys Leu Ser Asp Ala Asp Lys Ile Ser
                245                 250                 255
Asn Tyr Lys Lys Asp Gly Lys Asn Asp Lys Phe Val Gly Leu Val Ala
                260                 265                 270
Asp Ser Val Gln Met Lys Gly Ile Asn Gln Tyr Ile Ile Phe Tyr Lys
                275                 280                 285
Pro Lys Pro Thr Ser Phe Ala Arg Phe Arg Arg Ser Ala Arg Ser Arg
            290                 295                 300
Arg Ser Leu Pro Ala Glu Met Pro Leu Ile Pro Val Asn Gln Ala Asp
305                 310                 315                 320
Thr Leu Ile Val Asp Gly Glu Ala Val Ser Leu Thr Gly His Ser Gly
                325                 330                 335
Asn Ile Phe Ala Pro Glu Gly Asn Tyr Arg Tyr Leu Thr Tyr Gly Ala
                340                 345                 350
Glu Lys Leu Pro Gly Gly Ser Tyr Ala Leu Arg Val Gln Gly Glu Pro
            355                 360                 365
Ala Lys Gly Glu Met Leu Ala Gly Ala Ala Val Tyr Asn Gly Glu Val
            370                 375                 380
Leu His Phe His Thr Glu Asn Gly Arg Pro Tyr Pro Thr Arg Gly Arg
385                 390                 395                 400
Phe Ala Ala Lys Val Asp Phe Gly Ser Lys Ser Val Asp Gly Ile Ile
                405                 410                 415
Asp Ser Gly Asp Asp Leu His Met Gly Thr Gln Lys Phe Lys Ala Ala
                420                 425                 430
Ile Asp Gly Asn Gly Phe Lys Gly Thr Trp Thr Glu Asn Gly Ser Gly
            435                 440                 445
Asp Val Ser Gly Lys Phe Tyr Gly Pro Ala Gly Glu Glu Val Ala Gly
            450                 455                 460
Lys Tyr Ser Tyr Arg Pro Thr Asp Ala Glu Lys Gly Gly Phe Gly Val
465                 470                 475                 480
Phe Ala Gly Lys Lys Glu Gln Asp
            485

<210> SEQ ID NO 10
<211> LENGTH: 364
<212> TYPE: PRT
<213> ORGANISM: Neisseria meningitidis

<400> SEQUENCE: 10

Met Ser Met Lys His Phe Pro Ser Lys Val Leu Thr Thr Ala Ile Leu
1               5                   10                  15
Ala Thr Phe Cys Ser Gly Ala Leu Ala Ala Thr Ser Asp Asp Asp Val
                20                  25                  30
```

```
Lys Lys Ala Ala Thr Val Ala Ile Val Ala Ala Tyr Asn Asn Gly Gln
             35                  40                  45

Glu Ile Asn Gly Phe Lys Ala Gly Glu Thr Ile Tyr Asp Ile Gly Glu
 50                  55                  60

Asp Gly Thr Ile Thr Gln Lys Asp Ala Thr Ala Ala Asp Val Glu Ala
 65                  70                  75                  80

Asp Asp Phe Lys Gly Leu Gly Leu Lys Lys Val Val Thr Asn Leu Thr
                 85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 11
<211> LENGTH: 174
<212> TYPE: PRT
<213> ORGANISM: Neisseria meningitidis

<400> SEQUENCE: 11

Met Lys Lys Ala Leu Ala Thr Leu Ile Ala Leu Ala Leu Pro Ala Ala
 1               5                  10                  15

Ala Leu Ala Glu Gly Ala Ser Gly Phe Tyr Val Gln Ala Asp Ala Ala
             20                  25                  30

His Ala Lys Ala Ser Ser Ser Leu Gly Ser Ala Lys Gly Phe Ser Pro
         35                  40                  45
```

-continued

```
Arg Ile Ser Ala Gly Tyr Arg Ile Asn Asp Leu Arg Phe Ala Val Asp
            50                  55                  60

Tyr Thr Arg Tyr Lys Asn Tyr Lys Ala Pro Ser Thr Asp Phe Lys Leu
 65                  70                  75                  80

Tyr Ser Ile Gly Ala Ser Ala Ile Tyr Asp Phe Asp Thr Gln Ser Pro
                    85                  90                  95

Val Lys Pro Tyr Leu Gly Ala Arg Leu Ser Leu Asn Arg Ala Ser Val
                100                 105                 110

Asp Leu Gly Gly Ser Asp Ser Phe Ser Gln Thr Ser Ile Gly Leu Gly
                115                 120                 125

Val Leu Thr Gly Val Ser Tyr Ala Val Thr Pro Asn Val Asp Leu Asp
            130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170
```

<210> SEQ ID NO 12
<211> LENGTH: 591
<212> TYPE: PRT
<213> ORGANISM: Neisseria meningitidis

<400> SEQUENCE: 12

```
Met Asn Lys Ile Tyr Arg Ile Ile Trp Asn Ser Ala Leu Asn Ala Trp
 1               5                  10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
 50                  55                  60

Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
            130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Asp Thr Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
                210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
```

-continued

```
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
        275                 280                 285
Val Thr Gly Lys Asp Lys Gly Glu Asn Gly Ser Ser Thr Asp Glu Gly
    290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
        355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
        435                 440                 445
Ser Val Ser Leu Gly Ala Gly Ala Asp Ala Pro Thr Leu Ser Val Asp
    450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
Val Asp Gly Asn Ala Arg Ala Gly Ile Ala Gln Ala Ile Ala Thr Ala
        515                 520                 525
Gly Leu Val Gln Ala Tyr Leu Pro Gly Lys Ser Met Met Ala Ile Gly
    530                 535                 540
Gly Gly Thr Tyr Arg Gly Glu Ala Gly Tyr Ala Ile Gly Tyr Ser Ser
545                 550                 555                 560
Ile Ser Asp Gly Gly Asn Trp Ile Ile Lys Gly Thr Ala Ser Gly Asn
                565                 570                 575
Ser Arg Gly His Phe Gly Ala Ser Ala Ser Val Gly Tyr Gln Trp
            580                 585                 590

<210> SEQ ID NO 13
<211> LENGTH: 1457
<212> TYPE: PRT
<213> ORGANISM: Neisseria meningitidis

<400> SEQUENCE: 13

Met Lys Thr Thr Asp Lys Arg Thr Thr Glu Thr His Arg Lys Ala Pro
1               5                   10                  15
Lys Thr Gly Arg Ile Arg Phe Ser Pro Ala Tyr Leu Ala Ile Cys Leu
            20                  25                  30
```

```
Ser Phe Gly Ile Leu Pro Gln Ala Trp Ala Gly His Thr Tyr Phe Gly
         35                  40                  45

Ile Asn Tyr Gln Tyr Tyr Arg Asp Phe Ala Glu Asn Lys Gly Lys Phe
 50                  55                  60

Ala Val Gly Ala Lys Asp Ile Glu Val Tyr Asn Lys Lys Gly Glu Leu
 65              70                  75                  80

Val Gly Lys Ser Met Thr Lys Ala Pro Met Ile Asp Phe Ser Val Val
             85                  90                  95

Ser Arg Asn Gly Val Ala Ala Leu Val Gly Asp Gln Tyr Ile Val Ser
             100                 105                 110

Val Ala His Asn Gly Gly Tyr Asn Asn Val Asp Phe Gly Ala Glu Gly
         115                 120                 125

Arg Asn Pro Asp Gln His Arg Phe Thr Tyr Lys Ile Val Lys Arg Asn
130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                 165                 170                 175

Thr Ser Tyr Met Asp Gly Arg Lys Tyr Ile Asp Gln Asn Asn Tyr Pro
             180                 185                 190

Asp Arg Val Arg Ile Gly Ala Gly Arg Gln Tyr Trp Arg Ser Asp Glu
         195                 200                 205

Asp Glu Pro Asn Asn Arg Glu Ser Ser Tyr His Ile Ala Ser Ala Tyr
210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                 245                 250                 255

Phe Leu Pro Thr Gly Ser Phe Gly Asp Ser Gly Ser Pro Met Phe
             260                 265                 270

Ile Tyr Asp Ala Gln Lys Gln Lys Trp Leu Ile Asn Gly Val Leu Gln
         275                 280                 285

Thr Gly Asn Pro Tyr Ile Gly Lys Ser Asn Gly Phe Gln Leu Val Arg
290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                 325                 330                 335

Asn Gly Thr Gly Lys Ile Asn Ala Lys His Glu His Asn Ser Leu Pro
             340                 345                 350

Asn Arg Leu Lys Thr Arg Thr Val Gln Leu Phe Asn Val Ser Leu Ser
         355                 360                 365

Glu Thr Ala Arg Glu Pro Val Tyr His Ala Ala Gly Val Asn Ser
370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                 405                 410                 415

Gly Leu Tyr Phe Gln Gly Asp Phe Thr Val Ser Pro Glu Asn Asn Glu
             420                 425                 430

Thr Trp Gln Gly Ala Gly Val His Ile Ser Glu Asp Ser Thr Val Thr
         435                 440                 445

Trp Lys Val Asn Gly Val Ala Asn Asp Arg Leu Ser Lys Ile Gly Lys
```

```
            450             455             460
Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
                500                 505                 510

Val Gln Leu Asn Ala Asp Asn Gln Phe Asn Pro Asp Lys Leu Tyr Phe
                515                 520                 525

Gly Phe Arg Gly Gly Arg Leu Asp Leu Asn Gly His Ser Leu Ser Phe
                530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
                580                 585                 590

Asn Gly Trp Phe Gly Glu Lys Asp Thr Thr Lys Thr Asn Gly Arg Leu
                595                 600                 605

Asn Leu Val Tyr Gln Pro Ala Ala Glu Asp Arg Thr Leu Leu Leu Ser
                610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
                690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
                755                 760                 765

Asn Leu Thr Gly Leu Ala Thr Leu Asn Gly Asn Leu Ser Ala Asn Gly
                770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
                850                 855                 860

Val Phe His Phe Glu Ser Ser Arg Phe Thr Gly Gln Ile Ser Gly Gly
865                 870                 875                 880
```

```
Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
        915                 920                 925

Thr Asp Ala Pro Arg Arg Ser Arg Ser Arg Arg Ser Leu Leu
930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
        995                 1000                1005

Leu Glu Gln Leu Thr Val Val Glu Gly Lys Asp Asn Lys Pro Leu Ser
    1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
        1075                1080                1085

Ala Ala Gly Arg Asp Ala Val Glu Lys Thr Glu Ser Val Ala Glu Pro
    1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln
        1155                1160                1165

Pro Gln Arg Asp Leu Ile Ser Arg Tyr Ala Asn Ser Gly Leu Ser Glu
    1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
                1205                1210                1215

Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
    1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
                1285                1290                1295
```

```
Phe Ser Ser Gly Ser Leu Ser Asp Gly Ile Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
            1365                1370                1375

Pro Ala Gln His Ile Ser Ile Thr Pro Tyr Leu Ser Leu Ser Tyr Thr
            1380                1385                1390

Asp Ala Ala Ser Gly Lys Val Arg Thr Arg Val Asn Thr Ala Val Leu
            1395                1400                1405

Ala Gln Asp Phe Gly Lys Thr Arg Ser Ala Glu Trp Gly Val Asn Ala
            1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
            1445                1450                1455

Trp

<210> SEQ ID NO 14
<211> LENGTH: 797
<212> TYPE: PRT
<213> ORGANISM: Neisseria meningitidis

<400> SEQUENCE: 14

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205
```

-continued

Arg Ser Asn Gln Phe Asn Glu Gln Lys Phe Ala Gln Asp Met Glu Lys
210             215                 220

Val Thr Asp Phe Tyr Gln Asn Asn Gly Tyr Phe Asp Phe Arg Ile Leu
225             230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
                260                 265                 270

Glu Gly Asp Thr Asn Glu Val Pro Lys Ala Glu Leu Glu Lys Leu Leu
                275                 280                 285

Thr Met Lys Pro Gly Lys Trp Tyr Glu Arg Gln Gln Met Thr Ala Val
290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
                340                 345                 350

His Ile Thr Gly Asn Asn Lys Thr Arg Asp Glu Val Val Arg Arg Glu
                355                 360                 365

Leu Arg Gln Met Glu Ser Ala Pro Tyr Asp Thr Ser Lys Leu Gln Arg
370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
                420                 425                 430

Val Gln Asp Thr Gly Leu Val Met Ser Ala Gly Val Ser Gln Asp Asn
                435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Ala Gly
                500                 505                 510

Ala Gly Ile Arg Met Ser Val Pro Val Thr Glu Tyr Asp Arg Val Asn
                515                 520                 525

Phe Gly Leu Val Ala Glu His Leu Thr Val Asn Thr Tyr Asn Lys Ala
530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
                580                 585                 590

Thr Gly Val Asn Ala Glu Ile Ala Leu Pro Gly Ser Lys Leu Gln Tyr
                595                 600                 605

Tyr Ser Ala Thr His Asn Gln Thr Trp Phe Pro Leu Ser Lys Thr
610                 615                 620

Phe Thr Leu Met Leu Gly Gly Glu Val Gly Ile Ala Gly Gly Tyr Gly

```
                625                 630                 635                 640
Arg Thr Lys Glu Ile Pro Phe Phe Glu Asn Phe Tyr Gly Gly Leu
                    645                 650                 655
Gly Ser Val Arg Gly Tyr Glu Ser Gly Thr Leu Gly Pro Lys Val Tyr
                    660                 665                 670
Asp Glu Tyr Gly Glu Lys Ile Ser Tyr Gly Asn Lys Ala Asn
                675                 680                 685
Val Ser Ala Glu Leu Leu Phe Pro Met Pro Gly Ala Lys Asp Ala Arg
            690                 695                 700
Thr Val Arg Leu Ser Leu Phe Ala Asp Ala Gly Ser Val Trp Asp Gly
705                 710                 715                 720
Lys Thr Tyr Asp Asp Asn Ser Ser Ser Ala Thr Gly Gly Arg Val Gln
                725                 730                 735
Asn Ile Tyr Gly Ala Gly Asn Thr His Lys Ser Thr Phe Thr Asn Glu
                740                 745                 750
Leu Arg Tyr Ser Ala Gly Gly Ala Val Thr Trp Leu Ser Pro Leu Gly
                755                 760                 765
Pro Met Lys Phe Ser Tyr Ala Tyr Pro Leu Lys Lys Lys Pro Glu Asp
            770                 775                 780
Glu Ile Gln Arg Phe Gln Phe Gln Leu Gly Thr Thr Phe
785                 790                 795

<210> SEQ ID NO 15
<211> LENGTH: 6
<212> TYPE: PRT
<213> ORGANISM: Artificial Sequence
<220> FEATURE:
<223> OTHER INFORMATION: Linker

<400> SEQUENCE: 15

Gly Ser Gly Gly Gly Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Linker

<400> SEQUENCE: 16

Gly Ser Gly Ser Gly Gly Gly Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Poly-histidine tag

<400> SEQUENCE: 17

His His His His His His
1               5

<210> SEQ ID NO 18
<211> LENGTH: 2376
<212> TYPE: DNA
<213> ORGANISM: Neisseria meningitidis

<400> SEQUENCE: 18
```

```
atgaaaccat tacaaatgct ccctatcgcc gcgctggtcg gcagtatttt cggcaatccg    60
gtcttggcag cagatgaagc tgcaactgaa accacacccg ttaaggcaga gataaaagca   120
gtgcgcgtta aaggtcagcg caatgcgcct gcggctgtgg aacgcgtcaa ccttaaccgt   180
atcaaacaag aaatgatacg cgacaataaa gacttggtgc gctattccac cgatgtcggc   240
ttgagcgaca gcggccgcca tcaaaaaggc tttgctgttc gcggcgtgga aggcaaccgt   300
gtcggcgtga gcatagacgg tgtaaacctg cctgattctg aagaaaactc gctgtacgcc   360
cgttatggca acttcaacag ctcgcgtttg tctatcgacc ccgaactcgt gcgcaacatc   420
gaaatcgtga agggcgcaga ctcttttcaat accggcagtg gtgcattggg cggcggtgtg   480
aattaccaaa cgctgcaagg ccgtgatttg ctgttggacg acaggcaatt cggcgtgatg   540
atgaaaaacg gttacagcac gcgtaaccgt gaatggacaa atactctcgg tttcggtgtg   600
agtaacgacc gcgtggatgc tgctttgctg tattcgcaac gtcgcggtca tgaaaccgaa   660
agcgcgggaa accgaggcta tgctgtggaa ggggaaggca gtggcgcgaa tatccgtggt   720
tcggcacgcg gtatccctga ttcgtccaaa cacaaatacc acagcttttt gggtaagatt   780
gcttaccaaa ttaacgataa ccaccgcatc ggcgcatcgc ttaacggcca gcagggacat   840
aattacacgg ttgaagagtc ttataacctg accgcttctt cctggcgcga agccgatgac   900
gtaaacagac ggcgcaatgc caacctcttt tacgaatgga tgcctgattc aaattggttg   960
tcgtctttga aggcggactt cgattatcag aaaaccaaag tggcggcggt taacaacaaa  1020
ggctcgttcc cgatggatta ttccacctgg acgcgcaact ataatcagaa ggatttggac  1080
gaaatataca accgcagcat ggacacccga ttcaaacgtt ttacttttgcg tttggacagc  1140
catccgttgc aactcggggg ggggcgacac cgcctgtcgt ttaaaacttt cgtcagccgc  1200
cgtgattttg aaaacctaaa ccgcgacgat tattacttca gcggccgtgt tgttcgaacc  1260
accagcagta tccagcatcc ggtgaaaacc accaactacg gtttctcact gtctgaccaa  1320
attcaatgga acgacgtgtt cagtagccgc gcaggtatcc gttacgacca caccaaaatg  1380
acgcctcagg aattgaatgc cgagtgtcat gcttgtgaca aaacaccacc tgcagccaac  1440
acttataaag gctggagcgg ttttgtcggc ttggcggcgc aactgaatca ggcttggcat  1500
gtcggttacg acattacttc cggctaccgc gtccccaatg cgtccgaagt gtatttcacc  1560
tacaaccacg gttcgggtaa ttggctgcct aatcccaacc tgaaagccga gcgcagcacc  1620
acccacaccc tgtctctgca aggccgcagc gaaaaaggca tgctggatgc caacctgtat  1680
caaagcaatt accgcaattt cctgtctgaa gagcagaagc tgaccaccag cggcactccc  1740
ggctgtactg aggaaaatgc ttactacggt atatgcagcg acccctacaa agaaaaactg  1800
gattggcaga tgaaaaatat cgacaaggcc agaatccgcg gtatcgagct gacaggccgt  1860
ctgaatgtgg acaaagtagc gtcttttgtt cctgagggtt ggaaactgtt cggctcgctg  1920
ggttatgcga aaagcaaact gtcgggcgac aacagcctgc tgtccacaca gccgctgaaa  1980
gtgattgccg gtatcgacta tgaaagtccg agcgaaaaat ggggcgtatt ctcccgcctg  2040
acctatctgg gcgcgaaaaa ggccaaagat gcgcagtaca ccgtttatga aaacaagggc  2100
tggggtacgc ctttgcagaa aaaggtaaaa gattacccgt ggctgaacaa gtcggcttat  2160
gtgtttgata tgtacggctt ctacaaaccg gctaaaaacc tgactttgcg tgcaggcgta  2220
tataatgtgt tcaaccgcaa atacaccact tgggattccc tgcgcggcct gtatagctac  2280
agcaccacca actcggtcga ccgcgatggc aaaggcttag accgctaccg cgccccaagc  2340
cgtaattacg ccgtatcgct ggaatggaag tttttaa                           2376
```

```
<210> SEQ ID NO 19
<211> LENGTH: 791
<212> TYPE: PRT
<213> ORGANISM: Neisseria meningitidis

<400> SEQUENCE: 19

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Asn
    210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr His Ser Phe
                245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
        275                 280                 285

Asn Leu Thr Ala Ser Ser Trp Arg Glu Ala Asp Asp Val Asn Arg Arg
    290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Val Asn Asn Lys Gly Ser Phe Pro Met Asp Tyr Ser Thr Trp Thr Arg
            340                 345                 350

Asn Tyr Asn Gln Lys Asp Leu Asp Glu Ile Tyr Asn Arg Ser Met Asp
        355                 360                 365

Thr Arg Phe Lys Arg Phe Thr Leu Arg Leu Asp Ser His Pro Leu Gln
```

-continued

```
               370                 375                 380
Leu Gly Gly Arg His Arg Leu Ser Phe Lys Thr Phe Val Ser Arg
385                 390                 395                 400

Arg Asp Phe Glu Asn Leu Asn Arg Asp Asp Tyr Tyr Phe Ser Gly Arg
                405                 410                 415

Val Val Arg Thr Thr Ser Ser Ile Gln His Pro Val Lys Thr Thr Asn
                420                 425                 430

Tyr Gly Phe Ser Leu Ser Asp Gln Ile Gln Trp Asn Asp Val Phe Ser
                435                 440                 445

Ser Arg Ala Gly Ile Arg Tyr Asp His Thr Lys Met Thr Pro Gln Glu
    450                 455                 460

Leu Asn Ala Glu Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Asn
                485                 490                 495

Gln Ala Trp His Val Gly Tyr Asp Ile Thr Ser Gly Tyr Arg Val Pro
                500                 505                 510

Asn Ala Ser Glu Val Tyr Phe Thr Tyr Asn His Gly Ser Gly Asn Trp
                515                 520                 525

Leu Pro Asn Pro Asn Leu Lys Ala Glu Arg Ser Thr Thr His Thr Leu
    530                 535                 540

Ser Leu Gln Gly Arg Ser Glu Lys Gly Met Leu Asp Ala Asn Leu Tyr
545                 550                 555                 560

Gln Ser Asn Tyr Arg Asn Phe Leu Ser Glu Glu Gln Lys Leu Thr Thr
                565                 570                 575

Ser Gly Thr Pro Gly Cys Thr Glu Glu Asn Ala Tyr Tyr Gly Ile Cys
                580                 585                 590

Ser Asp Pro Tyr Lys Glu Lys Leu Asp Trp Gln Met Lys Asn Ile Asp
                595                 600                 605

Lys Ala Arg Ile Arg Gly Ile Glu Leu Thr Gly Arg Leu Asn Val Asp
    610                 615                 620

Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
                660                 665                 670

Lys Trp Gly Val Phe Ser Arg Leu Thr Tyr Leu Gly Ala Lys Lys Ala
                675                 680                 685

Lys Asp Ala Gln Tyr Thr Val Tyr Glu Asn Lys Gly Trp Gly Thr Pro
    690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Val Phe Asn Arg Lys Tyr Thr Thr Trp Asp
                740                 745                 750

Ser Leu Arg Gly Leu Tyr Ser Tyr Ser Thr Thr Asn Ser Val Asp Arg
                755                 760                 765

Asp Gly Lys Gly Leu Asp Arg Tyr Arg Ala Pro Ser Arg Asn Tyr Ala
    770                 775                 780

Val Ser Leu Glu Trp Lys Phe
785                 790
```

<210> SEQ ID NO 20
<211> LENGTH: 147
<212> TYPE: PRT
<213> ORGANISM: Neisseria meningitidis

<400> SEQUENCE: 20

Ala Asp Glu Ala Ala Thr Glu Thr Thr Pro Val Lys Ala Glu Ile Lys
1               5                   10                  15

Ala Val Arg Val Lys Gly Gln Arg Asn Ala Pro Ala Ala Val Glu Arg
            20                  25                  30

Val Asn Leu Asn Arg Ile Lys Gln Glu Met Ile Arg Asp Asn Lys Asp
        35                  40                  45

Leu Val Arg Tyr Ser Thr Asp Val Gly Leu Ser Asp Ser Gly Arg His
    50                  55                  60

Gln Lys Gly Phe Ala Val Arg Gly Val Glu Gly Asn Arg Val Gly Val
65                  70                  75                  80

Ser Ile Asp Gly Val Asn Leu Pro Asp Ser Glu Glu Asn Ser Leu Tyr
                85                  90                  95

Ala Arg Tyr Gly Asn Phe Asn Ser Ser Arg Leu Ser Ile Asp Pro Glu
            100                 105                 110

Leu Val Arg Asn Ile Glu Ile Val Lys Gly Ala Asp Ser Phe Asn Thr
        115                 120                 125

Gly Ser Gly Ala Leu Gly Gly Gly Val Asn Tyr Gln Thr Leu Gln Gly
    130                 135                 140

Arg Asp Leu
145

<210> SEQ ID NO 21
<211> LENGTH: 621
<212> TYPE: PRT
<213> ORGANISM: Neisseria meningitidis

<400> SEQUENCE: 21

Leu Leu Asp Asp Arg Gln Phe Gly Val Met Met Lys Asn Gly Tyr Ser
1               5                   10                  15

Thr Arg Asn Arg Glu Trp Thr Asn Thr Leu Gly Phe Gly Val Ser Asn
            20                  25                  30

Asp Arg Val Asp Ala Ala Leu Leu Tyr Ser Gln Arg Arg Gly His Glu
        35                  40                  45

Thr Glu Ser Ala Gly Asn Arg Gly Tyr Ala Val Glu Gly Glu Gly Ser
    50                  55                  60

Gly Ala Asn Ile Arg Gly Ser Ala Arg Gly Ile Pro Asp Ser Ser Lys
65                  70                  75                  80

His Lys Tyr His Ser Phe Leu Gly Lys Ile Ala Tyr Gln Ile Asn Asp
                85                  90                  95

Asn His Arg Ile Gly Ala Ser Leu Asn Gly Gln Gln Gly His Asn Tyr
            100                 105                 110

Thr Val Glu Glu Ser Tyr Asn Leu Thr Ala Ser Ser Trp Arg Glu Ala
        115                 120                 125

Asp Asp Val Asn Arg Arg Arg Asn Ala Asn Leu Phe Tyr Glu Trp Met
    130                 135                 140

Pro Asp Ser Asn Trp Leu Ser Ser Leu Lys Ala Asp Phe Asp Tyr Gln
145                 150                 155                 160

Lys Thr Lys Val Ala Ala Val Asn Asn Lys Gly Ser Phe Pro Met Asp
                165                 170                 175

```
Tyr Ser Thr Trp Thr Arg Asn Tyr Asn Gln Lys Asp Leu Asp Glu Ile
            180                 185                 190

Tyr Asn Arg Ser Met Asp Thr Arg Phe Lys Arg Phe Thr Leu Arg Leu
            195                 200                 205

Asp Ser His Pro Leu Gln Leu Gly Gly Gly Arg His Arg Leu Ser Phe
            210                 215                 220

Lys Thr Phe Val Ser Arg Arg Asp Phe Glu Asn Leu Asn Arg Asp Asp
225                 230                 235                 240

Tyr Tyr Phe Ser Gly Arg Val Val Arg Thr Thr Ser Ser Ile Gln His
                245                 250                 255

Pro Val Lys Thr Thr Asn Tyr Gly Phe Ser Leu Ser Asp Gln Ile Gln
            260                 265                 270

Trp Asn Asp Val Phe Ser Ser Arg Ala Gly Ile Arg Tyr Asp His Thr
            275                 280                 285

Lys Met Thr Pro Gln Glu Leu Asn Ala Glu Cys His Ala Cys Asp Lys
            290                 295                 300

Thr Pro Pro Ala Ala Asn Thr Tyr Lys Gly Trp Ser Gly Phe Val Gly
305                 310                 315                 320

Leu Ala Ala Gln Leu Asn Gln Ala Trp His Val Gly Tyr Asp Ile Thr
                325                 330                 335

Ser Gly Tyr Arg Val Pro Asn Ala Ser Glu Val Tyr Phe Thr Tyr Asn
            340                 345                 350

His Gly Ser Gly Asn Trp Leu Pro Asn Pro Asn Leu Lys Ala Glu Arg
            355                 360                 365

Ser Thr Thr His Thr Leu Ser Leu Gln Gly Arg Ser Glu Lys Gly Met
            370                 375                 380

Leu Asp Ala Asn Leu Tyr Gln Ser Asn Tyr Arg Asn Phe Leu Ser Glu
385                 390                 395                 400

Glu Gln Lys Leu Thr Thr Ser Gly Thr Pro Gly Cys Thr Glu Glu Asn
                405                 410                 415

Ala Tyr Tyr Gly Ile Cys Ser Asp Pro Tyr Lys Glu Lys Leu Asp Trp
            420                 425                 430

Gln Met Lys Asn Ile Asp Lys Ala Arg Ile Arg Gly Ile Glu Leu Thr
            435                 440                 445

Gly Arg Leu Asn Val Asp Lys Val Ala Ser Phe Val Pro Glu Gly Trp
450                 455                 460

Lys Leu Phe Gly Ser Leu Gly Tyr Ala Lys Ser Lys Leu Ser Gly Asp
465                 470                 475                 480

Asn Ser Leu Leu Ser Thr Gln Pro Leu Lys Val Ile Ala Gly Ile Asp
                485                 490                 495

Tyr Glu Ser Pro Ser Glu Lys Trp Gly Val Phe Ser Arg Leu Thr Tyr
            500                 505                 510

Leu Gly Ala Lys Lys Ala Lys Asp Ala Gln Tyr Thr Val Tyr Glu Asn
            515                 520                 525

Lys Gly Trp Gly Thr Pro Leu Gln Lys Val Lys Asp Tyr Pro Trp
            530                 535                 540

Leu Asn Lys Ser Ala Tyr Val Phe Asp Met Tyr Gly Phe Tyr Lys Pro
545                 550                 555                 560

Ala Lys Asn Leu Thr Leu Arg Ala Gly Val Tyr Asn Val Phe Asn Arg
                565                 570                 575

Lys Tyr Thr Thr Trp Asp Ser Leu Arg Gly Leu Tyr Ser Tyr Ser Thr
            580                 585                 590
```

Thr Asn Ser Val Asp Arg Asp Gly Lys Gly Leu Asp Arg Tyr Arg Ala
            595                 600                 605

Pro Ser Arg Asn Tyr Ala Val Ser Leu Glu Trp Lys Phe
    610                 615                 620

<210> SEQ ID NO 22
<211> LENGTH: 768
<212> TYPE: PRT
<213> ORGANISM: Neisseria meningitidis

<400> SEQUENCE: 22

Ala Asp Glu Ala Ala Thr Glu Thr Thr Pro Val Lys Ala Glu Ile Lys
1               5                   10                  15

Ala Val Arg Val Lys Gly Gln Arg Asn Ala Pro Ala Ala Val Glu Arg
            20                  25                  30

Val Asn Leu Asn Arg Ile Lys Gln Glu Met Ile Arg Asp Asn Lys Asp
        35                  40                  45

Leu Val Arg Tyr Ser Thr Asp Val Gly Leu Ser Asp Ser Gly Arg His
    50                  55                  60

Gln Lys Gly Phe Ala Val Arg Gly Val Glu Gly Asn Arg Val Gly Val
65              70                  75                  80

Ser Ile Asp Gly Val Asn Leu Pro Asp Ser Glu Asn Ser Leu Tyr
            85                  90                  95

Ala Arg Tyr Gly Asn Phe Asn Ser Ser Arg Leu Ser Ile Asp Pro Glu
            100                 105                 110

Leu Val Arg Asn Ile Glu Ile Val Lys Gly Ala Asp Ser Phe Asn Thr
        115                 120                 125

Gly Ser Gly Ala Leu Gly Gly Val Asn Tyr Gln Thr Leu Gln Gly
    130                 135                 140

Arg Asp Leu Leu Leu Asp Asp Arg Gln Phe Gly Val Met Met Lys Asn
145                 150                 155                 160

Gly Tyr Ser Thr Arg Asn Arg Glu Trp Thr Asn Thr Leu Gly Phe Gly
            165                 170                 175

Val Ser Asn Asp Arg Val Asp Ala Ala Leu Leu Tyr Ser Gln Arg Arg
        180                 185                 190

Gly His Glu Thr Glu Ser Ala Gly Asn Arg Gly Tyr Ala Val Glu Gly
    195                 200                 205

Glu Gly Ser Gly Ala Asn Ile Arg Gly Ser Ala Arg Gly Ile Pro Asp
    210                 215                 220

Ser Ser Lys His Lys Tyr His Ser Phe Leu Gly Lys Ile Ala Tyr Gln
225                 230                 235                 240

Ile Asn Asp Asn His Arg Ile Gly Ala Ser Leu Asn Gly Gln Gln Gly
            245                 250                 255

His Asn Tyr Thr Val Glu Glu Ser Tyr Asn Leu Thr Ala Ser Ser Trp
        260                 265                 270

Arg Glu Ala Asp Asp Val Asn Arg Arg Asn Ala Asn Leu Phe Tyr
    275                 280                 285

Glu Trp Met Pro Asp Ser Asn Trp Leu Ser Ser Leu Lys Ala Asp Phe
    290                 295                 300

Asp Tyr Gln Lys Thr Lys Val Ala Ala Val Asn Asn Lys Gly Ser Phe
305                 310                 315                 320

Pro Met Asp Tyr Ser Thr Trp Thr Arg Asn Tyr Asn Gln Lys Asp Leu
            325                 330                 335

Asp Glu Ile Tyr Asn Arg Ser Met Asp Thr Arg Phe Lys Arg Phe Thr
        340                 345                 350

```
Leu Arg Leu Asp Ser His Pro Leu Gln Leu Gly Gly Arg His Arg
        355                 360                 365
Leu Ser Phe Lys Thr Phe Val Ser Arg Arg Asp Phe Glu Asn Leu Asn
370                 375                 380
Arg Asp Asp Tyr Tyr Phe Ser Gly Arg Val Val Arg Thr Thr Ser Ser
385                 390                 395                 400
Ile Gln His Pro Val Lys Thr Thr Asn Tyr Gly Phe Ser Leu Ser Asp
                405                 410                 415
Gln Ile Gln Trp Asn Asp Val Phe Ser Ser Arg Ala Gly Ile Arg Tyr
                420                 425                 430
Asp His Thr Lys Met Thr Pro Gln Glu Leu Asn Ala Glu Cys His Ala
            435                 440                 445
Cys Asp Lys Thr Pro Pro Ala Ala Asn Thr Tyr Lys Gly Trp Ser Gly
        450                 455                 460
Phe Val Gly Leu Ala Ala Gln Leu Asn Gln Ala Trp His Val Gly Tyr
465                 470                 475                 480
Asp Ile Thr Ser Gly Tyr Arg Val Pro Asn Ala Ser Glu Val Tyr Phe
                485                 490                 495
Thr Tyr Asn His Gly Ser Gly Asn Trp Leu Pro Asn Pro Asn Leu Lys
                500                 505                 510
Ala Glu Arg Ser Thr Thr His Thr Leu Ser Leu Gln Gly Arg Ser Glu
            515                 520                 525
Lys Gly Met Leu Asp Ala Asn Leu Tyr Gln Ser Asn Tyr Arg Asn Phe
        530                 535                 540
Leu Ser Glu Glu Gln Lys Leu Thr Thr Ser Gly Thr Pro Gly Cys Thr
545                 550                 555                 560
Glu Glu Asn Ala Tyr Tyr Gly Ile Cys Ser Asp Pro Tyr Lys Glu Lys
                565                 570                 575
Leu Asp Trp Gln Met Lys Asn Ile Asp Lys Ala Arg Ile Arg Gly Ile
            580                 585                 590
Glu Leu Thr Gly Arg Leu Asn Val Asp Lys Val Ala Ser Phe Val Pro
        595                 600                 605
Glu Gly Trp Lys Leu Phe Gly Ser Leu Gly Tyr Ala Lys Ser Lys Leu
610                 615                 620
Ser Gly Asp Asn Ser Leu Leu Ser Thr Gln Pro Leu Lys Val Ile Ala
625                 630                 635                 640
Gly Ile Asp Tyr Glu Ser Pro Ser Glu Lys Trp Gly Val Phe Ser Arg
                645                 650                 655
Leu Thr Tyr Leu Gly Ala Lys Lys Ala Lys Asp Ala Gln Tyr Thr Val
            660                 665                 670
Tyr Glu Asn Lys Gly Trp Gly Thr Pro Leu Gln Lys Lys Val Lys Asp
        675                 680                 685
Tyr Pro Trp Leu Asn Lys Ser Ala Tyr Val Phe Asp Met Tyr Gly Phe
690                 695                 700
Tyr Lys Pro Ala Lys Asn Leu Thr Leu Arg Ala Gly Val Tyr Asn Val
705                 710                 715                 720
Phe Asn Arg Lys Tyr Thr Thr Trp Asp Ser Leu Arg Gly Leu Tyr Ser
                725                 730                 735
Tyr Ser Thr Thr Asn Ser Val Asp Arg Asp Gly Lys Gly Leu Asp Arg
            740                 745                 750
Tyr Arg Ala Pro Ser Arg Asn Tyr Ala Val Ser Leu Glu Trp Lys Phe
        755                 760                 765
```

<210> SEQ ID NO 23
<211> LENGTH: 915
<212> TYPE: PRT
<213> ORGANISM: Neisseria meningitidis

<400> SEQUENCE: 23

```
Met Gln Gln Gln His Leu Phe Arg Phe Asn Ile Leu Cys Leu Ser Leu
 1               5                  10                  15
Met Thr Ala Leu Pro Ala Tyr Ala Glu Asn Val Gln Ala Gly Gln Ala
            20                  25                  30
Gln Glu Lys Gln Leu Asp Thr Ile Gln Val Lys Ala Lys Lys Gln Lys
        35                  40                  45
Thr Arg Arg Asp Asn Glu Val Thr Gly Leu Gly Lys Leu Val Lys Ser
    50                  55                  60
Ser Asp Thr Leu Ser Lys Glu Gln Val Leu Asn Ile Arg Asp Leu Thr
65                  70                  75                  80
Arg Tyr Asp Pro Gly Ile Ala Val Val Glu Gln Gly Arg Gly Ala Ser
                85                  90                  95
Ser Gly Tyr Ser Ile Arg Gly Met Asp Lys Asn Arg Val Ser Leu Thr
            100                 105                 110
Val Asp Gly Val Ser Gln Ile Gln Ser Tyr Thr Ala Gln Ala Ala Leu
        115                 120                 125
Gly Gly Thr Arg Thr Ala Gly Ser Ser Gly Ala Ile Asn Glu Ile Glu
    130                 135                 140
Tyr Glu Asn Val Lys Ala Val Glu Ile Ser Lys Gly Ser Asn Ser Val
145                 150                 155                 160
Glu Gln Gly Ser Gly Ala Leu Ala Gly Ser Val Ala Phe Gln Thr Lys
                165                 170                 175
Thr Ala Asp Asp Val Ile Gly Glu Gly Arg Gln Trp Gly Ile Gln Ser
            180                 185                 190
Lys Thr Ala Tyr Ser Gly Lys Asn Arg Gly Leu Thr Gln Ser Ile Ala
        195                 200                 205
Leu Ala Gly Arg Ile Gly Gly Ala Glu Ala Leu Leu Ile His Thr Gly
    210                 215                 220
Arg Arg Ala Gly Glu Ile Arg Ala His Glu Asp Ala Gly Arg Gly Val
225                 230                 235                 240
Gln Ser Phe Asn Arg Leu Val Pro Val Glu Asp Ser Ser Asn Tyr Ala
                245                 250                 255
Tyr Phe Ile Val Lys Glu Glu Cys Lys Asn Gly Ser Tyr Glu Thr Cys
            260                 265                 270
Lys Ala Asn Pro Lys Lys Asp Val Val Gly Lys Asp Glu Arg Gln Thr
        275                 280                 285
Val Ser Thr Arg Asp Tyr Thr Gly Pro Asn Arg Phe Leu Ala Asp Pro
    290                 295                 300
Leu Ser Tyr Glu Ser Arg Ser Trp Leu Phe Arg Pro Gly Phe Arg Phe
305                 310                 315                 320
Glu Asn Lys Arg His Tyr Ile Gly Gly Ile Leu Glu His Thr Gln Gln
                325                 330                 335
Thr Phe Asp Thr Arg Asp Met Thr Val Pro Ala Phe Leu Thr Lys Ala
            340                 345                 350
Val Phe Asp Ala Asn Lys Lys Gln Ala Gly Ser Leu Pro Gly Asn Gly
        355                 360                 365
Lys Tyr Ala Gly Asn His Lys Tyr Gly Gly Leu Phe Thr Asn Gly Glu
    370                 375                 380
```

```
Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
                435                 440                 445

Asp Gly Ser Asp Lys Tyr Cys Arg Pro Ser Ala Asp Lys Pro Phe Ser
            450                 455                 460

Tyr Tyr Lys Ser Asp Arg Val Ile Tyr Gly Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Gly Ser Asn Leu Arg His
                500                 505                 510

Gln Asp Tyr Tyr Tyr Gln His Ala Asn Arg Ala Tyr Ser Ser Asn Thr
                515                 520                 525

Pro Pro Gln Asn Asn Gly Lys Lys Ile Ser Pro Asn Gly Ser Glu Thr
                530                 535                 540

Ser Pro Tyr Trp Val Thr Ile Gly Arg Gly Asn Val Val Thr Gly Gln
545                 550                 555                 560

Ile Cys Arg Leu Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
                580                 585                 590

Gly Arg Trp Ala Asp Val Gly Ala Gly Leu Arg Tyr Asp Tyr Arg Ser
                595                 600                 605

Thr His Ser Asp Asp Gly Ser Val Ser Thr Gly Thr His Arg Thr Leu
                610                 615                 620

Ser Trp Asn Ala Gly Ile Val Leu Lys Pro Thr Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ala Gly Val Gln Ser Lys Ala Val Lys Ile Asp Pro
                660                 665                 670

Glu Lys Ser Phe Asn Lys Glu Ala Gly Ile Val Phe Lys Gly Asp Phe
                675                 680                 685

Gly Asn Leu Glu Ala Ser Trp Phe Asn Asn Ala Tyr Arg Asp Leu Ile
                690                 695                 700

Val Arg Gly Tyr Glu Ala Gln Ile Lys Asp Gly Lys Glu Glu Ala Lys
705                 710                 715                 720

Gly Asp Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
                740                 745                 750

Glu Gly Trp Tyr Ser Thr Phe Ala Tyr Asn Arg Val Arg Val Arg Asp
                755                 760                 765

Ile Lys Lys Arg Ala Asp Arg Thr Asp Ile Gln Ser His Leu Phe Asp
                770                 775                 780

Ala Ile Gln Pro Ser Arg Tyr Val Val Gly Leu Gly Tyr Asp Gln Pro
785                 790                 795                 800
```

```
Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ala Arg Arg Thr Arg Pro Trp Tyr Ile Val
        835                 840                 845

Asp Val Ser Gly Tyr Tyr Thr Val Lys Lys His Phe Thr Leu Arg Ala
    850                 855                 860

Gly Val Tyr Asn Leu Leu Asn Tyr Arg Tyr Val Thr Trp Glu Asn Val
865                 870                 875                 880

Arg Gln Thr Ala Gly Gly Ala Val Asn Gln His Lys Asn Val Gly Val
            885                 890                 895

Tyr Asn Arg Tyr Ala Ala Pro Gly Arg Asn Tyr Thr Phe Ser Leu Glu
        900                 905                 910

Met Lys Phe
        915

<210> SEQ ID NO 24
<211> LENGTH: 712
<212> TYPE: PRT
<213> ORGANISM: Neisseria meningitidis

<400> SEQUENCE: 24

Met Asn Asn Pro Leu Val Asn Gln Ala Ala Met Val Leu Pro Val Phe
1               5                   10                  15

Leu Leu Ser Ala Cys Leu Gly Gly Gly Ser Phe Asp Leu Asp Ser
            20                  25                  30

Val Asp Thr Glu Ala Pro Arg Pro Ala Pro Lys Tyr Gln Asp Val Phe
        35                  40                  45

Ser Glu Lys Pro Gln Ala Gln Lys Asp Gln Gly Gly Tyr Gly Phe Ala
    50                  55                  60

Met Arg Leu Lys Arg Arg Asn Trp Tyr Pro Gln Ala Lys Glu Asp Glu
65                  70                  75                  80

Val Lys Leu Asp Glu Ser Asp Trp Glu Ala Thr Gly Leu Pro Asp Glu
            85                  90                  95

Pro Lys Glu Leu Pro Lys Arg Gln Lys Ser Val Ile Glu Lys Val Glu
        100                 105                 110

Thr Asp Ser Asp Asn Asn Ile Tyr Ser Ser Pro Tyr Leu Lys Pro Ser
    115                 120                 125

Asn His Gln Asn Gly Asn Thr Gly Asn Gly Ile Asn Gln Pro Lys Asn
130                 135                 140

Gln Ala Lys Asp Tyr Glu Asn Phe Lys Tyr Val Tyr Ser Gly Trp Phe
145                 150                 155                 160

Tyr Lys His Ala Lys Arg Glu Phe Asn Leu Lys Val Glu Pro Lys Ser
            165                 170                 175

Ala Lys Asn Gly Asp Asp Gly Tyr Ile Phe Tyr His Gly Lys Glu Pro
        180                 185                 190

Ser Arg Gln Leu Pro Ala Ser Gly Lys Ile Thr Tyr Lys Gly Val Trp
    195                 200                 205

His Phe Ala Thr Asp Thr Lys Lys Gly Gln Lys Phe Arg Glu Ile Ile
210                 215                 220

Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
            245                 250                 255
```

-continued

Gln Glu Gly Tyr Gly Phe Thr Ser Asn Leu Glu Val Asp Phe His Asn
            260                 265                 270

Lys Lys Leu Thr Gly Lys Leu Ile Arg Asn Asn Ala Asn Thr Asp Asn
            275                 280                 285

Asn Gln Ala Thr Thr Gln Tyr Tyr Ser Leu Glu Ala Gln Val Thr
    290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Leu
                325                 330                 335

Ser Gly Gly Phe Phe Gly Pro Gln Gly Glu Glu Leu Gly Phe Arg Phe
            340                 345                 350

Leu Ser Asp Asp Gln Lys Val Ala Val Val Gly Ser Ala Lys Thr Lys
            355                 360                 365

Asp Lys Pro Ala Asn Gly Asn Thr Ala Ala Ala Ser Gly Gly Thr Asp
            370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
                405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
            435                 440                 445

Gln Ala Asn Gln Gly Thr Asn Gly Gly Thr Ala Phe Thr Arg Lys Phe
    450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
            485                 490                 495

Lys Thr Lys Thr Tyr Glu Val Glu Val Cys Cys Ser Asn Leu Asn Tyr
            500                 505                 510

Leu Lys Tyr Gly Met Leu Thr Arg Lys Asn Ser Lys Ser Ala Met Gln
            515                 520                 525

Ala Gly Glu Ser Ser Ser Gln Ala Asp Ala Lys Thr Glu Gln Val Glu
530                 535                 540

Gln Ser Met Phe Leu Gln Gly Glu Arg Thr Asp Glu Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
            595                 600                 605

Gly Thr Leu Thr Ala Asp Asn Arg Gln Glu Ala Thr Phe Thr Ile Asp
            610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

```
Glu Glu Leu Gly Gly Trp Phe Ala Tyr Pro Gly Asp Lys Gln Thr Lys
            675                 680                 685

Asn Ala Thr Asn Ala Ser Gly Asn Ser Ser Ala Thr Val Val Phe Gly
            690                 695                 700

Ala Lys Arg Gln Gln Pro Val Arg
705                 710

<210> SEQ ID NO 25
<211> LENGTH: 186
<212> TYPE: PRT
<213> ORGANISM: Neisseria meningitidis

<400> SEQUENCE: 25

Met Asn Met Lys Thr Leu Leu Ala Leu Ala Val Ser Ala Val Cys Ser
1               5                   10                  15

Val Gly Val Ala Gln Ala His Glu His Asn Thr Ile Pro Lys Gly Ala
            20                  25                  30

Ser Ile Glu Val Lys Val Gln Gln Leu Asp Pro Val Asn Gly Asn Lys
            35                  40                  45

Asp Val Gly Thr Val Thr Ile Thr Glu Ser Asn Tyr Gly Leu Val Phe
        50                  55                  60

Thr Pro Asp Leu Gln Gly Leu Ser Glu Gly Leu His Gly Phe His Ile
65                  70                  75                  80

His Glu Asn Pro Ser Cys Glu Pro Lys Glu Lys Glu Gly Lys Leu Thr
                85                  90                  95

Ala Gly Leu Gly Ala Gly Gly His Trp Asp Pro Lys Gly Ala Lys Gln
            100                 105                 110

His Gly Tyr Pro Trp Gln Asp Asp Ala His Leu Gly Asp Leu Pro Ala
        115                 120                 125

Leu Thr Val Leu His Asp Gly Thr Ala Thr Asn Pro Val Leu Ala Pro
            130                 135                 140

Arg Leu Lys His Leu Asp Asp Val Arg Gly His Ser Ile Met Ile His
145                 150                 155                 160

Thr Gly Gly Asp Asn His Ser Asp His Pro Ala Pro Leu Gly Gly Gly
                165                 170                 175

Gly Pro Arg Met Ala Cys Gly Val Ile Lys
            180                 185
```